US012253520B2

(12) United States Patent
Schneider

(10) Patent No.: US 12,253,520 B2
(45) Date of Patent: *Mar. 18, 2025

(54) COMPOSITIONS AND METHODS FOR ASSAYING PLATELET REACTIVITY AND TREATMENT SELECTION

(71) Applicant: University of Vermont and State Agricultural College, Burlington, VT (US)

(72) Inventor: David Schneider, Burlington, VT (US)

(73) Assignee: University of Vermont and State Agricultural College

(*) Notice: Subject to any disclaimer, the term of this patent is extended or adjusted under 35 U.S.C. 154(b) by 0 days.

This patent is subject to a terminal disclaimer.

(21) Appl. No.: 18/353,683

(22) Filed: Jul. 17, 2023

(65) Prior Publication Data

US 2023/0358744 A1  Nov. 9, 2023

Related U.S. Application Data

(60) Continuation of application No. 16/668,397, filed on Oct. 30, 2019, now Pat. No. 11,747,335, which is a division of application No. 14/403,337, filed as application No. PCT/US2013/042540 on May 23, 2013, now Pat. No. 10,502,737.

(60) Provisional application No. 61/651,779, filed on May 25, 2012.

(51) Int. Cl.
*G01N 33/53* (2006.01)
*A61K 31/4365* (2006.01)
*A61K 31/443* (2006.01)
*A61K 31/519* (2006.01)
*G01N 33/569* (2006.01)
*G01N 33/68* (2006.01)
*G01N 33/86* (2006.01)

(52) U.S. Cl.
CPC ... *G01N 33/56966* (2013.01); *A61K 31/4365* (2013.01); *A61K 31/443* (2013.01); *A61K 31/519* (2013.01); *G01N 33/6854* (2013.01); *G01N 33/86* (2013.01); *G01N 2333/70535* (2013.01); *G01N 2800/222* (2013.01); *G01N 2800/226* (2013.01); *G01N 2800/52* (2013.01)

(58) Field of Classification Search
None
See application file for complete search history.

(56) References Cited

U.S. PATENT DOCUMENTS

| 4,313,734 A | 2/1982 | Leuvering |
| 4,657,760 A | 4/1987 | Kung et al. |
| 4,816,567 A | 3/1989 | Cabilly et al. |
| 4,956,778 A | 9/1990 | Naito |
| 5,091,513 A | 2/1992 | Huston et al. |
| 5,132,405 A | 7/1992 | Huston et al. |
| 5,206,344 A | 4/1993 | Katre et al. |
| 5,225,212 A | 7/1993 | Martin et al. |
| 5,225,539 A | 7/1993 | Winter |
| 5,530,101 A | 6/1996 | Queen et al. |
| 5,585,089 A | 12/1996 | Queen et al. |
| 5,656,611 A | 8/1997 | Kabanov et al. |
| 5,693,762 A | 12/1997 | Queen et al. |
| 5,753,613 A | 5/1998 | Ansell et al. |
| 5,785,992 A | 7/1998 | Ansell et al. |
| 5,800,979 A | 9/1998 | Kolhouse et al. |
| 5,859,205 A | 1/1999 | Adair et al. |
| 6,120,798 A | 9/2000 | Allen et al. |
| 6,221,959 B1 | 4/2001 | Kabanov et al. |
| 6,346,613 B1 | 2/2002 | O'Mahony et al. |
| 6,353,055 B1 | 3/2002 | Kabanov et al. |
| 7,425,421 B2 | 9/2008 | Dertinger |
| 7,439,079 B2 | 10/2008 | Song et al. |
| 9,683,038 B2 | 6/2017 | Thuren et al. |
| 9,803,243 B2 | 10/2017 | Sharp et al. |
| 10,502,737 B2 | 12/2019 | Schneider |
| 11,747,335 B2 * | 9/2023 | Schneider ............ A61K 31/443 436/501 |
| 2002/0142305 A1 | 10/2002 | Chin et al. |
| 2003/0003469 A1 | 1/2003 | Stinchcomb et al. |
| 2005/0023454 A1 | 2/2005 | Bateman et al. |
| 2005/0035286 A1 | 2/2005 | Bajic et al. |
| 2005/0042620 A1 | 2/2005 | Hampel et al. |
| 2005/0196754 A1 | 9/2005 | Drmanac et al. |
| 2006/0105419 A1 | 5/2006 | Blankenberg et al. |
| 2007/0185053 A1 | 8/2007 | Linn |
| 2009/0081228 A1 * | 3/2009 | Lau ........................ C07K 16/18 424/139.1 |

(Continued)

FOREIGN PATENT DOCUMENTS

CN  203829101 U  9/2014
JP  2012-505660 A  3/2012

(Continued)

OTHER PUBLICATIONS

Schlitt et al., Effects of combined therapy of clopidogrel and aspirin in preventing thrombus formation on mechanical heart valves in ex vivo rabbit model, Thrombosis Research, 107, 2002, pp. 39-43. (Year: 2002).*

(Continued)

*Primary Examiner* — Gary Counts
(74) *Attorney, Agent, or Firm* — Quarles & Brady LLP

(57) ABSTRACT

Compositions and methods are provided for determining platelet reactivity where the levels of FcγRIIa on the surface of platelets is measured and if the levels of FcγRIIa are greater than a reference value, the platelets have enhanced reactivity.

19 Claims, 23 Drawing Sheets

Specification includes a Sequence Listing.

(56) References Cited

U.S. PATENT DOCUMENTS

| | | |
|---|---|---|
| 2011/0144170 A1 | 6/2011 | Hogarth et al. |
| 2014/0356356 A1 | 12/2014 | Thuren et al. |
| 2015/0160213 A1 | 6/2015 | Schneider et al. |
| 2015/0164053 A1 | 6/2015 | Chen et al. |
| 2020/0166508 A1 | 5/2020 | Schneider |
| 2021/0231682 A1 | 7/2021 | Schneider et al. |

FOREIGN PATENT DOCUMENTS

| | | |
|---|---|---|
| JP | 2017-537103 A | 12/2017 |
| WO | WO 2003023354 A2 | 3/2003 |
| WO | WO 2004058747 A1 | 7/2004 |
| WO | WO 2008043566 A2 | 4/2008 |
| WO | WO 2010075861 A2 | 7/2010 |
| WO | WO 2011082319 A1 | 7/2011 |
| WO | WO 2013177473 A1 | 11/2013 |
| WO | WO 2014087240 A2 | 6/2014 |
| WO | WO 2017186908 A1 | 11/2017 |
| WO | WO 2019204308 A1 | 10/2019 |

OTHER PUBLICATIONS

Eikelboom et al., Combined antiplatelet and anticoagulant therapy: clinical benefits and risks, Journal of Thrombosis and Haemostasis, 5, Suppl. 1, 2007, pp. 255-263. (Year: 2007).*

National Library of Medicine, National Center for Biotechnology Information, Homo sapiens Fc fragment of IgG receptor IIa (FCGR2A), transcript variant 1, mRNA, NCBI Reference Sequence: NM_001136219.1, May 19, 2019, https://www.ncbi.nlm.nih.gov/nuccore/NM_001136219.1, 5 pages.

National Library of Medicine, National Center for Biotechnology Information, low affinity immunoglobulin gamma Fc region receptor II-a isoform 1 precursor [Homo sapiens], NCBI Reference Sequence: NM_001129691.1, Aug. 19, 2024, https://www.ncbi.nlm.nih.gov/protein/NP_001129691.1, 5 pages.

NM_001136219.1, downloaded Aug. 10, 2023, https://www.ncbi.nlm.nih.gov/nuccore/NM_001136219.1, 5 pages.

NP_001129691.1, downloaded Aug. 10, 2023, from https://www.ncbi.nlm.nih.gov/protein/NP_001129691.1, 5 pages.

Achyuthan et al., "Gly-Pro-Arg-Pro modifies the glutamine residues in the a- and y-chains of fibrinogen: inhibition of wansglutaminase cross-linking," Biochimica et Biophysica Acta (BBA)-Protein Structure and Molecular Enzymology, Aug. 15, 1986, vol. 872, No. 3, pp. 261-268.

Aggarwal et al., wBiphasic Effects of Hemodialysis on Platelet Reactivity in Patients With End-Stage Renal Disease: A Potential Contributor to Cardiovascular Risk, American Journal of Kidney Diseases, Aug. 2002, vol. 40, No. 2, pp. 315-322.

Al-Horani et al., "Factor XIa inhibitors: A review of the patent literature" Expert Opin Ther Pat. 2016;26(3):323-45.

Benton et al. "Screening λgt recombinant clones by hybridization to single plaques in situ." Science 196.4286(1977): 180-182.

Berge et al., "Pharmaceutical salts" J Pharm Sci. Jan. 1977;66(1):1-19.

Bittl et al., Duration of Dual Antiplatelet Therapy: A Systemic Review for the 2016 ACC/AHA Guideline Focused Update on Duration of Dual Antiplatelet Therapy in Patients With Coronary Artery Disease,w Circulation, vol. 134, pp. e156-e178, Sep. 6, 2016.

Boylan et al., "Identification of FcλRIIa as the ITAM-bearing receptor mediating αIIβ83 outside-in integrin signaling in human platelets." Blood, The Journal of the American Society of Hematology 112.7 (2008): 2780-2786.

Breet et al., "Comparison of Platelet Function Tests in Predicting Clinical Outcome in Patients Undergoing Coronary Stent Implantation," JAMA, vol. 303, No. 8, pp. 754-762; Feb. 24, 2010.

Brummelkamp et al., "A system for stable expression of short interfering RNAs in mammalian cells" Science. Apr. 19, 2002;296(5567):550-3.

Calverley et al., Potential role of platelet FcγRIIA in collagen-mediated platelet activation associated with 1:1therothrombosis,w Atherosclerosis, 2002, vol. 164, No. 2, pp. 261-267.

Canobbio et al., "A new role for FcγRIIA in the potentiation of human platelet activation induced by weak Stimulation," Cellular Signalling, 2006, vol. 18, No. 6, pp. 861-870.

Chi et al., Dual antithrombotic plus adjunctive antiinflammatory therapy to improve cardiovascular outcome in atrial fibrillation patients with concurrent acute coronary syndrome: A triple-pathway strategy, Medical Hypotheses, Mar. 2018, vol. 114, pp. 40-44.

Chong et al., "Increased Expression of Platelet IgG Fc Receptors in Immune Heparin-Induced Thrombocytopenia," Slood, Feb. 15, 1993, vol. 81, No. 4, pp. 988-993.

Clemetson et al., The Platelet Collagen Receptor Glycoprotein VI is a Member of the Immunoglobulin Superfamily Closely Related to FcaR and the Natural Killer Receptors,w The Journal of Biological Chemistry, Oct. 8, 1999, vol. 274, No. 41, pp. 29019-29024.

Collet et al., "Bedside Monitoring to Adjust Antiplatelet Therapy for Coronary Stenting," The New England Journal of Medicine, vol. 367, pp. 2100-2109; Nov. 4, 2012.

Costanzi et al. "In Guide to Molecular Cloning Techniques, Berger SL, Kimmel AR, eds." (1987): 582-587.

Elbashir et al., "Duplexes of 21-nucleotide RNAs mediate RNA interference in cultured mammalian cells." nature 411.6836 (2001): 494-498.

El-Shahawy et al., Platelet FcγRIIA Receptor Surface Expression is Increased in Patients With ESRD and is Associated With Atherosclerotic Cardiovascular Events, American Journal of Kidney Diseases, Jan. 2007, vol. 49, No.1, pp. 127-134.

Fischer et al., "What is a minor stroke?" Stroke. Apr. 2010;41(4):661-6.

Goldhaber et al., Treatment of Blood Clots,w Circulation, Nov. 12, 2002, vol. 106, No. 20, pp. e138-e140.

Gousset et al., Evidence for a Physiological Role for Membrane Rafts in Human Platelets,w Journal of Cellular Physiology, 2002, vol. 190, No. 1, pp. 117-128.

Greinacher et al. "Clinical features of heparin-induced thrombocytopenia including risk factors for thrombosis." Thrombosis and haemostasis 94.07 (2005): 132-135.

Gruber et al., "Efficient tumor cell lysis mediated by a bispecific single chain antibody expressed in Escherichia coli" J Immunol, Jun. 1, 1994;152(11):5368-74.

Grunstein et al.,"Colony hybridization: a method for the isolation of cloned DNAs that contain a specific gene." Proceedings of the National Academy of Sciences 72.10 (1975): 3961-3965.

Hampel et al., "Hairpin' catalytic RNA model: evidence for helices and sequence requirement for substrate RNA" Nucleic Acids Res. Jan. 25, 1990;18(2):299-304.

Hampel et al., "RNA catalytic properties of the minimum (−)sTRSV sequence" Biochemistry. Jun. 13, 1989:28(12):4929-33.

Hannon "RNA interference" Nature. Jul. 11, 2002:418(6894):244-51.

Haseloff et al., "Simple RNA enzymes with new and highly specific endoribonuclease activities" Nature. Aug. 18, 1988;334(6183):585-91.

Hochholzer et al., Variability of Individual Platelet Reactivity Over Time in Patients Treated With Clopidogrel, Journal Pf the American College of Cardiology, vol. 64, No. 4, pp. 361-368; Jul. 29, 2014.

Holliger et al., "Diabodies: small bivalent and bispecific antibody fragments" Proc Natl Acad Sci U S A. Jul. 15, 1993;90(14):6444-8.

Huston et al., "Protein engineering of antibody binding sites: recovery of specific activity in an anti-digoxin single-chain Fv analogue produced in Escherichia coli" Proc Natl Acad Sci U S A. Aug. 1988;85(16):5879-83.

Hutvagner et al., "RNAi: nature abhors a double-strand" Curr Opin Genet Dev. Apr. 2002;12(2):225-32.

Kabbani et al., wPlatelet Reactivity Characterized Prospectively: A Determinant of Outcome 90 Days After Percutaneous Coronary Intervention, Circulation, Jul. 10, 2001, vol. 104, No. 2, pp. 181-186.

Karas et al., "Characterization of the IgG-Fc receptor on human platelets" Blood. Dec. 1982;60(6):1277-82.

(56) References Cited

OTHER PUBLICATIONS

Kay et al., "Quantitative flow cytometry of ZAP-70 levels in chronic lymphocytic leukemia using molecules of equivalent soluble fluorochrome" Cytometry B Clin Cytom. Jul. 15, 2006;70(4):218-26.

Khorana et al., "Development and validation of a predictive model for chemotherapy-associated thrombosis" Blood. May 15, 2008;111(10):4902-7.

Kimmel "[54] Identification and characterization of specific clones: Strategy for confirming the validity of presumptive clones." Methods in Enzymology. vol. 152. Academic Press, 1987. 507-511.

Kostelny et al., "Formation of a bispecific antibody by the use of leucine zippers" J Immunol. Mar. 1, 1992;148(5):1547-53.

Langer et al., "New methods of drug delivery" Science. Sep. 28, 1990;249(4976):1527-33.

Lee et al., "Expression of small interfering RNAs targeted against HIV-1 rev transcripts in human cells" Nat Biotechnol. May 2002;20(5):500-5.

Lee et al., "Lipid rafts facilitate the interaction of PECAM-1 with the glycoprotein VI-FcR gamma-chain complex in human platelets" J Biol Chem. Dec. 22, 2006;281(51):39330-8.

Liebeskind et al. "Endothelial Shear Stress and Platelet FcγRIIa Expression in Intracranial Atherosclerotic Disease." Frontiers in neurology 12 (2021): 646309. 7 pages.

Lippi et al., "Sample collection and platelet function testing: influence of vacuum or aspiration principle on PFA-100 test results" Blood Coagul Fibrinolysis. Sep. 2013;24(6):666-9.

Looney et al., Identification of a Second Class of IgG Fe Receptors on Human Neutrophils: A 40 Kilodalton Molecule 1:11so Found on Eosinophils,w Journal of Experimental Medicine, Apr. 1986, vol. 163, No. 4, pp. 826-836.

Lova et al.,"A Gi-dependent pathway is required for activation of the small GTPase Rap1B in human platelets" J Biol Chem . Apr. 5, 2002;277(14):12009-15.

Madsen et al., "Influence of preparative procedures on assay of platelet function and apparent effects of antiplatelet agents" Am J Cardiol. Aug. 15, 2007:100(4):722-7.

McCaffrey et al., "RNA interference in adult mice." Nature 418. 6893 (2002): 38-39.

McMahon et al., Variation in platelet expression of FcyRlla after myocardial infarction, Journal of Thrombosis and Irhrombolysis, vol. 48, pp. 88-94; 2019.

Mehran et al., "Standardized bleeding definitions for cardiovascular clinical trials: a consensus report from the Bleeding Academic Research Consortium"Circulation. Jun. 14, 2011;123(23):2736-47.

Miyagishi et al., "U6 promoter-driven siRNAs with four uridine 3' overhangs efficiently suppress targeted gene expression in mammalian cells" Nat Biotechnol. May 2002;20(5):497-500.

Moriarty et al., P-TU-033: *Escherichia coli*-induced platelet aggregation; Journal of Thrombosis and Haemostasis. Jul. 2011, vol. 9, Suppl. 2, p. 318.

Murray et al., "Regulation of thromboxane receptor activation in human platelets." Proceedings of the National Academy of Sciences 86.1 (1989): 124-128.

Paddison et al., "Short hairpin RNAs (shRNAs) induce sequence-specific silencing in mammalian cells." Genes & development 16.8 (2002): 948-958.

Pasalic et al., "Novel assay demonstrates that coronary artery disease patients have heightened procoagulant platelet response" J Thromb Haemost. Jun. 2018;16(6):1198-1210.

Patel et al., "Conceptual Framework for Addressing Residual Atherosclerotic Cardiovascular Disease Risk in the Era ol Precision Medicine," Circulation, vol. 137, pp. 2551-2553; Jun. 12, 2018.

Paul et al., "Effective expression of small interfering RNA in human cells" Nat Biotechnol. May 2002; 20(5):505-8.

Pedicord et al., "CD32-dependent platelet activation by a drug-dependent antibody to glycoprotein llb/llla lmtagonists," Thrombosis and Haemostasis, 2003, vol. 89, No. 3, pp. 513-521.

Power et al., "Generation of recombinant multimeric antibody fragments for tumor diagnosis and therapy" Methods Mol Biol. 2003;207:335-50.

Price et al., "Standard- vs High-Dose Clopidogrel Based on Platelet Function Testing After Percutaneous Coronary intervention," JAMA, vol. 305, No. 11, pp. 1097-1105; Mar. 16, 2011.

Quadrini et al., "Validation of a flow cytometry-based assay to assess C5aR receptor occupancy on neutrophils and monocytes for use in drug development" Cytometry B Clin Cytom. Mar. 2016; 90(2):177-90.

Raaz-Schrauder et al., "Patients with unstable angina pectoris show an increased frequency of the Fc gamma RIIa R131 allele." Autoimmunity 45.7 (2012): 556-564.

Rand et al., "Blood clotting in minimally altered whole blood." (1996): 3432-3445.

Reilly et al., "Heparin-Induced Thrombocytopenia/Thrombosis in a Transgenic Mouse Model Requires Human Platelet Factor 4 and Platelet Activation Through FcγRIIA," Blood, The American Society of Hematology, U.S., Oct. 15, 2001, vol. 98, No. 8, pp. 2442-2447.

Roper et al., "Retention of prom in in in microvilli reveals distinct cholesterol-based lipid micro-domains in the apical plasma membrane," Nature Cell Biology, Sep. 2000, vol. 2, pp. 582-592.

Rossi et al., "Ribozymes as anti-HIV-1 therapeutic agents: principles, applications, and problems" AIDS Res Hum Retroviruses. Feb. 1992:8(2):183-9.

Sacco et al., "An updated definition of stroke for the 21st century: a statement for healthcare professionals from the American Heart Association/American Stroke Association" Stroke. Jul. 2013;44(7):2064-89.

Schneider et al., "FcγRIIa: A New Cardiovascular Risk Marker" J Am Coll Cardiol. Jul. 10, 2018;72(2):237-238.

Schneider et al., "Differential effects of anticoagulants on the activation of platelets ex vivo." Circulation 96.9(1997): 2877-2883.

Schneider et al., Association Between Increased Platelet P-Selectin Expression and Obesity in Patients Wrth Type e Diabetes: A BARI 2D (Bypass Angioplasty Revascularization Investigation 2 Diabetes) substudy; Diabetes Care, May 2009, vol. 32, No. 5, pp. 944-949.

Schneider et al., "Increased reactivity of platelets induced by fibrinogen independent of its binding to the IIb-IIIa surface glycoprotein: a potential contributor to cardiovascular risk." Journal of the American College of Cardiology 33.1 (1999): 261-266.

Schneider et al., "Time and Dose Dependent Augmentation of Inhibitory Effects of Abciximab by Aspirin." Ifhrombosis and Haemostasis. 2001, vol. 85, No. 2, pp. 309-313.

Serrano et al., "Increased platelet expression of FcGammaRlla and its potential impact on platelet reactivity in patients with end stage renal disease," Thrombosis Journal. Jun. 4, 2007, vol. 5, Article No. 7, pp. 1-7.

Sharp et al., "RNA interference—2001" Genes Dev. Mar. 1, 2001;15(5):485-90.

Sibbing et al., "Updated expert consensus statement on platelet function and genetic testing for guiding P2Y12 receptor inhibitor treatment in percutaneous coronary intervention." JACC: Cardiovascular Interventions 12.16 (2019): 1521-1537.

Stolla et al., "CalDAG-GEFl deficiency protects mice in a novel model of Fcγ RIIA-mediated thrombosis and thrombocytopenia" Blood. Jul. 28, 2011:118(4):1113-20.

Steyerberg et al., "Internal validation of predictive models: efficiency of some procedures for logistic regression analysis" J Clin Epidemiol. Aug. 2001:54(8):774-81.

Storey et al., Effects of P2Y1 and P2Y12 receptor antagonists on platelet aggregation induced by different agonists n human whole blood; Platelets, 2001, vol. 12, No. 7, pp. 443-447.

Strambo et al., "Defining minor symptoms in acute ischemic stroke" Cerebrovasc Dis. 2015:39(3-4):209-15.

Sui et al., "A DNA vector-based RNAi technology to suppress gene expression in mammalian cells" Proc Natl Acad Sci U S A. Apr. 16, 2002;99(8):5515-20.

Torzewski et al., "Animal models of C-reactive protein." Mediators of inflammation 2014 (2014). pp. 1-7.

(56) References Cited

OTHER PUBLICATIONS

Tuschl "RNA interference and small interfering RNAs" Chembiochem. Apr. 2, 2001;2(4):239-45.

Tutt et al., "Trispecific F(ab40 )3 derivatives that use cooperative signaling via the TCR/CD3 complex and CD2 to activate and redirect resting cytotoxic T cells" J Immunol. Jul. 1, 1991;147(1):60-9.

Van Der Vekiens et al., Human and equine cardiovascular endocrinology: beware to compare, Cardiovascular Endocrinology 2013, vol 2, No. 4, pp. 67-76. (Year: 2013).

Villanueva et al., "Automated serum peptide profiling." Nature protocols 1.2 (2006): 880-891.

Voora et al., "A freeze on tailored antiplatelet therapy?." Circulation 129.21 (2014): 2088-2090.

Wahl et al., "[43] Molecular hybridization of immobilized nucleic acids: Theoretical concepts and practical considerations." Methods in enzymology. vol. 152. Academic Press, 1987. 399-407.

Wahl et al., "Improved radio imaging and tumor localization with monoclonal F(ab')2" J Nucl Med. Apr. 1983;24(4):316-25.

Williams et al., "Inflammatory mechanisms of diabetic complications" Curr Diab Rep. Jun. 2007; 7(3):242-8.

Wiviott et al., "Prasugrel compared with high loading-and maintenance-dose clopidogrel in patients with planned percutaneous coronary intervention: the Prasugrel in Comparison to Clopidogrel for Inhibition of Platelet Activation and Aggregation-Thrombolysis in Myocardial Infarction 44 trial." Circulation 116.25 (2007): 2923-2932.

Wu et al., "Anti-carcinoembryonic antigen (CEA) diabody for rapid tumor targeting and imaging." Tumor Targeting 4 (1999): 47-58.

Yu et al., "RNA interference by expression of short-interfering RNAs and hairpin RNAs in mammalian cells" Proc Natl Acad Sci U S A. Apr. 30, 2002;99(9):6047-52.

Zamore et al., "RNAi: double-stranded RNA directs the ATP-dependent cleavage of mRNA at 21 to 23 nucleotide intervals" Cell. Mar. 31, 2000;101(1):25-33.

Zapata et al., "Engineering linear F(ab40 )2 fragments for efficient production in *Escherichia coli* and enhanced antiproliferative activity" Protein Eng. Oct. 1995;8(10):1057-62.

Zhai et al., "Prevention and Treatment of Venous Thromboembolism Associated with Coronavirus Disease 2019 Infection: A Consensus Statement before Guidelines" Thromb Haemost. Jun. 2020;120(6):937-948.

Communication pursuant to Article 94(3) EPC, relevant to foreign application No. 13793724.9, dated Apr. 3, 2017 (4 pages).

Communication pursuant to Article 94(3), relevant to foreign application No. 13793724.9, dated Feb. 5, 2018 (18 pages).

Decision to Refuse dated May 28, 2021 in corresponding European Patent Application No. 13793724.9 (16 pages).

Extended and Supplementary European Search Report with European Search Opinion for corresponding European Patent Application No. 13793724.9; issued Feb. 1, 2016 (8 pages).

International Search Report and Written Opinion for corresponding PCT Patent Application No. PCT/US2019/027684, dated Aug. 5, 2019 (10 pages).

International Search Report PCT/US2013/042540, mailed Aug. 21, 2013, (3 pages).

International Search Report and Written Opinion of Related PCT/US2021/044439, mailed Dec. 17, 2021, (10 pages).

International Search Report and Written Opinion of Related PCT/US2022/074502, mailed Dec. 6, 2022, (10 pages).

Office Action dated Apr. 12, 2021 in corresponding European Patent Application No. 13793724.9 (7 pages).

Office Action for corresponding European Patent Application No. 13793724.9, mailed Nov. 7, 2019 (5 pages).

Office Action in corresponding European Application No. 13793724.9, (5 pages).

* cited by examiner

Inflammation and Expression of FcγRIIa

| Cytokines | Growth Factors |
|---|---|
| tumor necrosis factor a | transforming growth factor |
| interleukin 1b | platelet-derived growth factor |
| interleukin 6 | epidermal growth factor |
| interleukin 10 | fibroblast growth factor |
| interleukin 19 | insulin-like growth factor 1 |
| interleukin 20 | |
| interleukin 22 | |
| interferon γ | |

The Effect of Interferon γ (50 ng/ml) on Monocytic and Myelocytic Cell Line Expression of FcγRIIa

COMPOSITIONS AND METHODS FOR ASSAYING PLATELET REACTIVITY AND TREATMENT SELECTION

CROSS-REFERENCE TO RELATED APPLICATIONS

This application is a continuation of U.S. patent application Ser. No. 16/668,397, filed Oct. 30, 2019 now U.S. Pat. No. 11,747,335, which is a divisional of U.S. patent application Ser. No. 14/403,337, filed Nov. 24, 2014, now U.S. Pat. No. 10,502,737, which is a U.S. national phase application pursuant to 35 U.S.C. § 371, of PCT International Application No. PCT/US2013/042540, filed May 23, 2013, designating the United States, which claims the benefit of and priority to U.S. Provisional Patent Application No. 61/651,779, filed May 25. 2012, all of which are incorporated herein by reference in their entirety.

REFERENCE TO AN ELECTRONIC SEQUENCE LISTING

The instant application contains a sequence listing which has been filed electronically and the contents of the electronic sequence listing (179429.00022.xml; Size: 6,481 bytes; and Date of Creation: Jul. 12, 2023) is herein incorporated by reference in its entirety.

BACKGROUND OF THE INVENTION

Increased platelet reactivity contributes to a greater risk of thrombosis, the proximate cause of heart attack and stroke. Given the negative health effects of thrombosis, assays for platelet reactivity should be useful for identifying individuals who are at risk of thrombosis, and in selecting appropriate therapeutic regimens. However, current assays of platelet reactivity have not demonstrated that capacity and are sensitive to medications and other therapies which are in common use. Therefore, novel assays for platelet reactivity that can guide therapy and are insensitive to common therapies and medications are needed.

SUMMARY OF THE INVENTION

As described below, the present invention features compositions and methods for assaying platelet reactivity. In general, blood is taken from an individual in a suitable anticoagulant. Platelets will be fixed. Subsequently an antibody that binds to FcγRIIa (e.g., primary antibody conjugated with a detectable label) and/or a secondary conjugated antibody will be added. The sample is analyzed with the use of flow cytometry. Platelets are identified by their characteristic size and the mean fluorescence intensity reflecting the surface expression of FcγRIIa will be quantified. Expression of FcγRIIa greater than the predefined threshold will be used to identify patients with elevated expression of FcγRIIa and increased platelet reactivity.

In one aspect, the invention provides a method of identifying a subject (e.g., human) with increased platelet reactivity involving determining a level of FcγRIIa on platelets from the subject; and comparing the level of FcγRIIa on the platelets with a reference value where an increased level compared to the reference value indicates that the subject has increased platelet reactivity.

In another aspect, the invention provides a method of identifying a subject (e.g., human) having an increased risk of thrombosis involving determining a level of FcγRIIa expressed on platelets from the subject; and comparing the level of FcγRIIa on the platelets with a reference value where an increased level compared to the reference value indicates that the subject has an increased risk of thrombosis.

In yet another aspect, the invention provides a method of determining platelet reactivity involving determining a level of FcγRIIa expressed on platelets from a subject, and comparing the level of FcγRIIa on the platelets with a reference value where an increased level compared to the reference is indicative of increased platelet reactivity.

In yet another aspect, the invention provides a method of selecting anti-thrombotic therapy in a subject involving determining a level of FcγRIIa expressed on platelets from the subject, and comparing the level of FcγRIIa to a reference value where an increased level compared to the reference value is indicative of a need for anti-thrombotic therapy or additional anti-thrombotic therapy. In one embodiment, the anti-thrombotic therapy is selected from the group consisting of prasugrel, ticagrelor, clopidogrel, and vorapaxar.

In yet another aspect, the invention provides a kit for determining platelet reactivity containing an FcγRIIa specific reagent and instructions for use of the kit in the method of any of of the above-aspects.

In yet another aspect, the invention provides a method of inhibiting platelet activation involving administering to a subject in need thereof an effective amount of an agent that inhibits FcγRIIa activation, thereby inhibiting platelet activation. In one embodiment, the agent is any one or more of a small molecule, an inhibitory nucleic acid, and an antibody or antigen-binding fragment thereof. In another embodiment, the inhibitory nucleic acid is any one or more of an antisense molecule, an shRNA, and an siRNA. In one embodiment, the inhibitory nucleic acid reduces the levels of FcγRIIa in megakaryoctes. In another embodiment, the subject is determined to be in need if platelets obtained from the subject have increased levels of FcγRIIa compared to a reference value.

In yet another aspect, the invention provides a test device for detecting FcγRIIa in a liquid sample, the device having a liquid permeable material defining the following portions in capillary communication: a) a first portion that is the site for application of a liquid sample, including a liquid permeable medium, and an FcγRIIa-binding conjugate; b) a second portion including a liquid permeable medium; and c) a third portion that is the site for detecting the binding of the FcγRIIa-binding conjugate at the test site, the third portion including a liquid permeable medium having the FcγRIIa fixed to the medium at the test site.

In a related aspect, the invention provides a method of determining platelet reactivity involving: determining a level of FcγRIIa expressed on platelets using a test device of the invention, and comparing the level of FcγRIIa on the platelets with a reference value where an increased level compared to the reference is indicative of increased platelet reactivity.

In another related aspect, the invention provides a method for detecting FcγRIIa in a liquid sample, the method involving: a) applying a liquid sample to a device of the invention; and b) detecting presence or absence of an FcγRIIa-binding conjugate at a test site, where the absence of the FcγRIIa-binding conjugate at the test site identifies the presence of FcγRIIa in the sample and the presence of FcγRIIa-binding conjugate at the test site identifies the absence of the FcγRIIa in the sample.

In a related aspect, the invention provides a kit comprising a test device of the invention. In various embodiments, the kit includes instructions for the use of the device for the detection of an analyte. In other embodiments, the kit includes a means for measuring a liquid sample and a test vial.

In yet another aspect, the invention provides a composition or kit for identifying and treating a subject having increased platelet reactivity, the composition including an FcγRIIa specific reagent and directions for using the reagent to measure the level of FcγRIIa in a biological sample of a subject, where a level greater than about 7,500 copies of FcγRIIa per platelet identifies the subject as having increased platelet reactivity; and (b) a therapeutic reagent that is one or more of prasugrel, ticagrelor, clopidogrel, and vorapaxar.

In various embodiments of the above-aspects or any other aspect of the invention delineated herein, the reference value is a level of FcγRIIa on the surface of platelets from a disease-free individual. In one embodiment, the reference value is about 5,000-6,000 copies of FcγRIIa per platelet and the increased level is 7,500, 8,000, 9,000, or 10,000 copies of FcγRIIa per platelet. In another embodiment, the increased level is about 10,000-20,000 copies of FcγRIIa per platelet. In another embodiment, the increased level is about 12,000-15,000 copies of FcγRIIa per platelet. In another embodiment, the level of FcγRIIa is determined using an FcγRIIa specific reagent. In another embodiment, the FcγRIIa specific reagent is an antibody or antigen-binding fragment thereof. In another embodiment, the level of platelet FcγRIIa is determined using an assay selected from the group consisting of flow cytometry, immunoassay, ELISA, western blotting, and radioimmunoassay. In another embodiment, the level of FcγRIIa is determined using fluorometric or colorimetric assay. In still other embodiments, the level of FcγRIIa is determined using flow cytometry. In still other embodiments, the reference value represents a level of FcγRIIa on platelets from disease-free subjects. In still other embodiments, the increased level is increased by at least about 1.5-5 fold, 2-5 fold, 5-10-fold, or 10-25 fold. In yet another embodiment, the reference value is 6,000 copies of FcγRIIa per platelet and the increased level is 8,000-20,000 or 10,000-20,000 copies of FcγRIIa per platelet. In various embodiments, the level of FcγRIIa is determined using an FcγRIIa specific reagent. In particular embodiments, the FcγRIIa specific reagent or FcγRIIa-binding conjugate is an antibody or antigen-binding fragment thereof. In various embodiments, the anti-thrombotic therapy is one or more of prasugrel, ticagrelor, clopidogrel, and vorapaxar.

In various embodiments of any of the aspects delineated herein, the first portion of the test device further contains a control conjugate; and the third portion of the test device contains a control conjugate binder present at a control site for detecting the binding of the control conjugate. In additional embodiments, the analyte-binding conjugate and the control conjugate coat the surface of the liquid permeable membrane in the first portion. In other embodiments, the coating is absent from the sample application site. In additional embodiments, the test device further includes a fourth portion that acts as a wick, the fourth portion including sorbent material. In other embodiments, the second portion of the test device includes a liquid permeable material that acts as a filter to remove particulates. In still other embodiments, the first portion of the test device contains a conjugate that specifically binds platelets. In various embodiments, the conjugate that specifically binds platelets is one or more of an antibody to glycoprotein (GP) IIb, GP MA, GP V, GP Ib, GP IX, a lysosomal membrane protein, and platelet endothelial cell adhesion molecule (PECAM). In particular embodiments, the conjugate that specifically binds platelets is one or more of anti-CD41, anti-CD41a, anti-CD61, anti-CD42d, anti-CD42b, anti-CD42a, anti-CD63, and anti-CD31. In still other embodiments, the second portion of the test device includes an agent that alters the composition of the liquid as it contacts the second portion.

The invention provides compositions and methods for assaying platelet reactivity. Compositions and articles defined by the invention were isolated or otherwise manufactured in connection with the examples provided below. Other features and advantages of the invention will be apparent from the detailed description, and from the claims.

Definitions

By "platelet reactivity" is meant the sensitivity of platelets to activation and clotting.

By "FcγRIIa" is meant the low affinity immunoglobulin gamma Fc region receptor II-a. An illustrative amino acid sequence of the FcγRIIa is provided at GenBank Accession No. NP_001129691.1"

```
  1    mtmetqmsqn vcprnlwllq pltvllllas adsqaaappk avlkleppwi nvlqedsvtl
 61    tcqgarspes dsiqwfhngn lipthtqpsy rfkannndsg eytcqtgqts lsdpvhltvl
121    sewlvlqtph lefqegetim lrchswkdkp lvkvtffqng ksqkfshldp tfsipqanhs
181    hsgdyhctgn igytlfsskp vtitvqvpsm gssspmgiiv avviatavaa ivaavvaliy
241    crkkrisans tdpvkaaqfe ppgrqmiair krqleetnnd yetadggymt lnpraptddd
301    kniyltlppn dhvnsnn.
```

An illustrative nucleic acid sequence encoding FcγRIIa is provided at GenBank Accession No. NM_001136219.1:

```
ATGACTATGGAGACCCAAATGTCTCAGAATGTATGTCCCAGAAACCTGT

GGCTGCTTCAACCATTGACAGTTTTGCTGCTGCTGGCTTCTGCAGACAG

TCAAGCTGCAGCTCCCCCAAAGGCTGTGCTGAAACTTGAGCCCCCGTGG

ATCAACGTGCTCCAGGAGGACTCTGTGACTCTGACATGCCAGGGGGCTC

GCAGCCCTGAGAGCGACTCCATTCAGTGGTTCCACAATGGGAATCTCAT

TCCCACCCACACGCAGCCCAGCTACAGGTTCAAGGCCAACAACAATGAC

AGCGGGGAGTACACGTGCCAGACTGGCCAGACCAGCCTCAGCGACCCTG

TGCATCTGACTGTGCTTTCCGAATGGCTGGTGCTCCAGACCCCTCACCT

GGAGTTCCAGGAGGGAGAAACCATCATGCTGAGGTGCCACAGCTGGAAG

GACAAGCCTCTGGTCAAGGTCACATTCTTCCAGAATGGAAAATCCCAGA
```

-continued

```
AATTCTCCCATTTGGATCCCACCTTCTCCATCCCACAAGCAAACCACAG

TCACAGTGGTGATTACCACTGCACAGGAAACATAGGCTACACGCTGTTC

TCATCCAAGCCTGTGACCATCACTGTCCAAGTGCCCAGCATGGGCAGCT

CTTCACCAATGGGGATCATTGTGGCTGTGGTCATTGCGACTGCTGTAGC

AGCCATTGTTGCTGCTGTAGTGGCCTTGATCTACTGCAGGAAAAAGCGG

ATTTCAGCCAATTCCACTGATCCTGTGAAGGCTGCCCAATTTGAGCCAC

CTGGACGTCAAATGATTGCCATCAGAAAGAGACAACTTGAAGAAACCAA

CAATGACTATGAAACAGCTGACGGCGGCTACATGACTCTGAACCCCAGG

GCACCTACTGACGATGATAAAAACATCTACCTGACTCTTCCTCCCAACG

ACCATGTCAACAGTAATAACTAA.
```

By "FcγRIIa specific agent" is meant any small molecule compound, antibody, nucleic acid molecule, or polypeptide, or fragments thereof that specifically bind to FcγRIIa.

By "flow cytometry" is meant a technique for counting and examining microscopic particles that allows for multi-parametric analysis of the physical and/or chemical characteristics of the microscopic particles.

By "Protease-activated receptor (PAR)" is meant a G protein-coupled receptor that is activated by cleavage of a portion of its extracellular domain. PARs are highly expressed in platelets, including the thrombin receptors PAR1, PAR3 and PAR4. PARs are activated by the action of serine proteases such as thrombin (e.g., activating PARs 1, 3 and 4). Cleavage of the N-terminus of the receptor, generates a tethered ligand (SFLLRN) that acts as an agonist, causing a physiological response. The cellular effects of thrombin are mediated by protease-activated receptors (PARs). Thrombin signaling in platelets contributes to hemostasis and thrombosis. Thrombin receptor antagonists include Vorapaxar (SCH 530348) which is a PAR1 antagonist.

By "Adenosine diphosphate (ADP) receptor" is meant a purinergic G protein-coupled receptors, stimulated by the nucleotide Adenosine diphosphate (ADP). ADP receptors include $P2Y_{12}$ which regulates thrombosis. Adenosine diphosphate (ADP) receptor antagonists are agents that inhibit adenosine diphosphate receptors. $P2Y_{12}$ is the target of the anti-platelet drugs including prasugrel, clopidogrel, and other thienopyridines.

By "clopidogrel" is meant (+)-(S)-methyl 2-(2-chlorophenyl)-2-(6,7-dihydrothieno[3,2-c]pyridin-5(4H)-yl)acetate which is a potent platelet aggregation inhibitor.

By "prasugrel" is meant (RS)-5-[2-cyclopropyl-1-(2-fluorophenyl)-2-oxoethyl]-4,5,6,7-tetrahydrothieno[3,2-c]pyridine-2-yl acetate which is a potent platelet aggregation inhibitor.

By "ticagrelor" is meant (1S,2S,3R,5S)-3-[7-[[(1R,2S)-2-(3,4-Difluorophenyl)cyclopropylamino]-5-(propylthio)-3H-[1,2,3]triazolo[4,5-d]pyrimidin-3-yl]-5-(2-hydroxyethoxy)cyclopentane-1,2-diol which is a potent platelet aggregation inhibitor.

By "vorapaxar" is meant Ethyl N-[(3R,3aS,4S,4aR,7R,8aR,9aR)-4-[(E)-2-[5-(3-fluorophenyl)-2-pyridyl]vinyl]-3-methyl-1-oxo-3a,4,4a,5,6,7,8,8a,9,9a-decahydro-3H-benzo[f]isobenzofuran-7-yl]carbamate which is a potent platelet aggregation inhibitor.

By "anti-thrombotic therapy" is meant any treatment used to inhibit platelet aggregation in a subject.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "analyte" is meant any compound under investigation using an analytical method.

By "analyte-binding conjugate" is meant a detectable molecule that binds a compound under investigation.

By "capillary communication" is meant facilitating the flow of a liquid between liquid permeable materials.

By "capture reagent" is meant a reagent that specifically binds a polypeptide or nucleic acid molecule to select or isolate the polypeptide or nucleic acid molecule. In various embodiments, the capture reagent for an FcγRIIa polypeptide is an anti-FcγRIIa antibody. In other embodiments, a platelet capture reagent specifically binds a platelet cell surface polypeptide (e.g., useful for binding platelets to a solid phase). Exemplary platelet capture reagents include without limitation antibodies to glycoprotein (GP) IIb (e.g., anti-CD41 or CD41a; antibodies to GP IIIa (e.g., anti-CD61); antibodies to GP V (e.g., anti-CD42d); antibodies to GP Ib (e.g., anti-CD42b); antibodies to GP IX such as anti-CD42a; antibodies to lysosomal membrane proteins (e.g., anti-CD63); antibodies to PECAM (e.g., anti-CD31).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "a control conjugate" is meant a detectable molecule that does not substantially bind a compound under investigation.

"Detect" refers to identifying the presence, absence or amount of the analyte to be detected.

By "detectable label" is meant a composition that when linked to a molecule of interest renders the latter detectable, via spectroscopic, photochemical, biochemical, immuno-chemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include thrombotic disease associated with an undesirable increase in platelet reactivity and/or the formation of a thrombus, such as a thrombus that results in an ischemic event.

By "effective amount" is meant the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat a thrombotic disease or disorder characterized by the methods delineated herein (e.g., characterized by an undesirable increase in platelet reactivity). In addition, the methods of the invention provide a facile means to identify therapies that are safe for use in subjects. In addition, the methods of the invention provide a route for analyzing virtually any number of compounds for effects on a thrombotic disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "lateral flow device" is meant a test device that relies on the flow of a liquid via capillary action, wicking, or wetting a liquid permeable media present in the device.

By "liquid permeable material" is meant a material susceptible to wetting, wicking, or transport of a liquid by capillary action.

By "marker" is meant any protein or polynucleotide having an alteration in expression level or activity that is associated with a disease or disorder. For example, an increase in FcγRIIa level, activity, phosphorylation, or expression is associated with increased platelet reactivity and/or an increased propensity to develop a thrombotic disease or disorder.

By "portion" is meant some fraction of a whole. A portion of a test device, for example, may be 0.1, 0.2, 0.3, 0.4, 0.5, 0.6, 0.7, 0.8, 0.9 of the length of the interior flow path of the device.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100% in a parameter.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100. mu·g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "test device" is meant a device used in the detection of an analyte in a sample.

By "wick" is meant sorb a liquid.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2A is a western blot of an anti-phosphotyrosine immunoprecipitate showing that FcγRIIa is phosphorylated following platelet activation with thrombin. Tyrosine phosphorylated proteins (FIG. 2A) were isolated by immunoprecipitation with the use of an anti-phosphotyrosine antibody (4G10) from platelet lysates ($2\times10^8$ platelets) exposed to no agonist or thrombin (50 nM) for 3 min. Western blots of immunoprecipitated proteins in lanes 1 and 2 and a non-selected platelet lysate in lane 3 were probed with anti-FcγRIIa. Anti-FcγRIIa identified tyrosine phosphorylated proteins at 45 kDa, 55 kDa, 75 kDa, and 90 kDa. FIG. 2B is a representative gel of a lipid raft preparation showing results with non-activated (control) and activated (convulxin 10 ng/ml) platelets ($4\times108$ in 0.5 ml). Platelets were lysed after 1.5 min and lipid rafts were prepared (sucrose gradient). Lipid rafts were identified with the use of cholera toxin B (CTB). FcγRIIa was immunoprecipitated and Western blots were probed with an anti-phosphotyrsine antibody (4G10), stripped, and re-probed with anti-FcγRIIa. Bands were identified with the use of chemiluminescence.

FIG. 5D shows the effect of tirofiban (0.5 µg/ml) on the activation of platelets (from n=3 subjects) identified by the surface expression of P-selectin. Tirofiban did not attenuate agonist-induced P-selectin expression, but consistent with its mechanism of action, tirofiban abolished binding of PAC-1 to platelets. Results are means±SD. Differences were identified with the use of paired Student's t test.

FIG. 8A is a graph showing that platelets from patients with coronary artery disease (CAD) or end stage renal disease (ESRD) have higher levels of FcγRIIa relative to healthy controls. FIG. 8B is a graph showing that platelets from patients with coronary artery disease (CAD) and 1 or more myocardial infarctions (MI) have higher levels of FcγRIIa relative to healthy controls.

DETAILED DESCRIPTION OF THE INVENTION

Figure 1A:
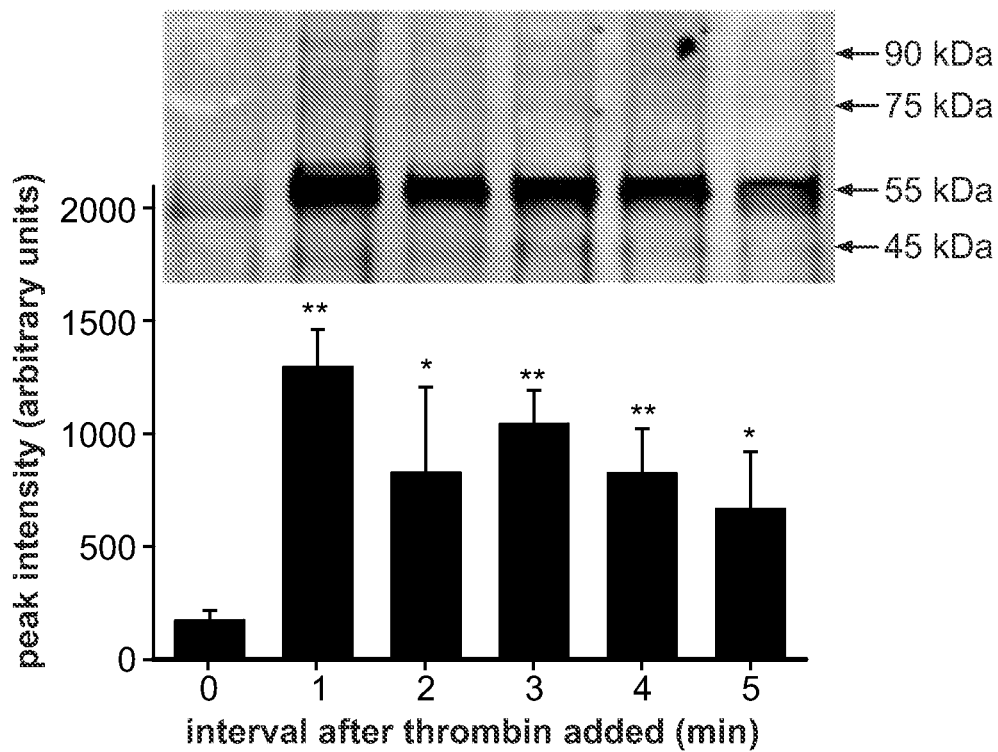
FIGS. 1A-1E are western blots and graphs showing that platelet activation results in FcγRIIa being phosphorylated: Platelets ($2\times10^8$ in 0.5 ml) from healthy subjects isolated with the use of gel filtration were exposed to no agonist (FIG. 1E) or to thrombin (50 nM)(FIG. 1A), convulxin (10 ng/ml) (FIG. 1B), ADP (25 µM)(FIG. 1C), and PAF (100 nM)(FIG. 1D) for selected intervals before preparation of platelet lysates. FcγRIIa was separated by immunoprecipitation and Western blots were probed with an antiphosphotyrosine antibody (4G10), stripped, and re-probed with anti-FcγRIIa to confirm equal loading (data not show). Fluorescence intensity of bands was quantified with the use of a Li-Cor system. Results (n=3-5 for each condition) are peak intensity that is not altered by adjusting the contrast of the image or the size of the area of interest, and were compared with those obtained when no agonist was used (Student's t test, *$p<0.05$, **$p<0.01$). The inset shows a representative gel probed with the anti-phosphotyrosine antibody. In addition to the expected band at 45 kDa, bands at 55 kDa, 75 kDa, and 90 kDa showed evidence of phosphorylation. Activation with each agonist led to phosphorylation of FcγRIIa after 3 minutes. Results with thrombin and PAF were apparent earlier than those with ADP.
Figure 1B:
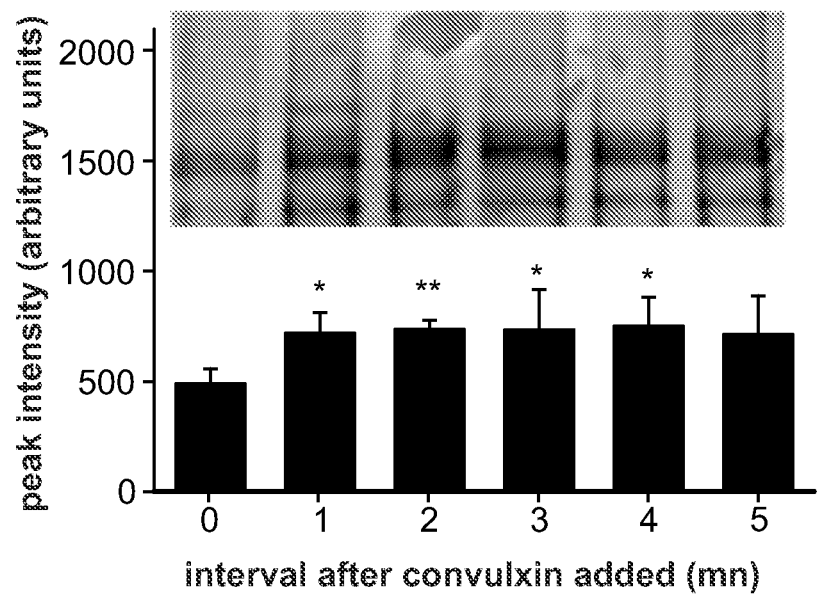
Figure 1C:
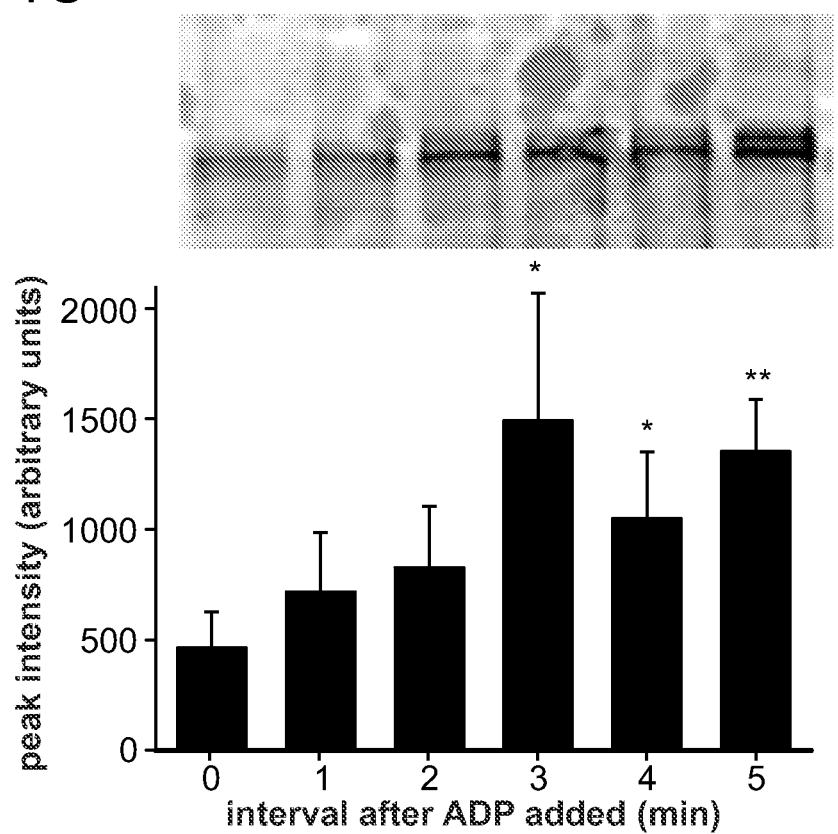
Figure 1D:
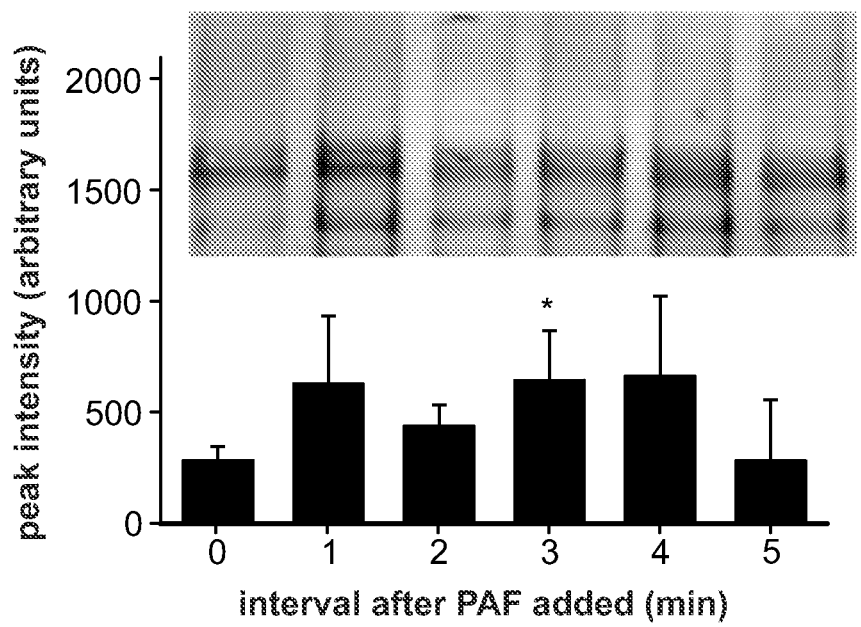
Figure 1E:
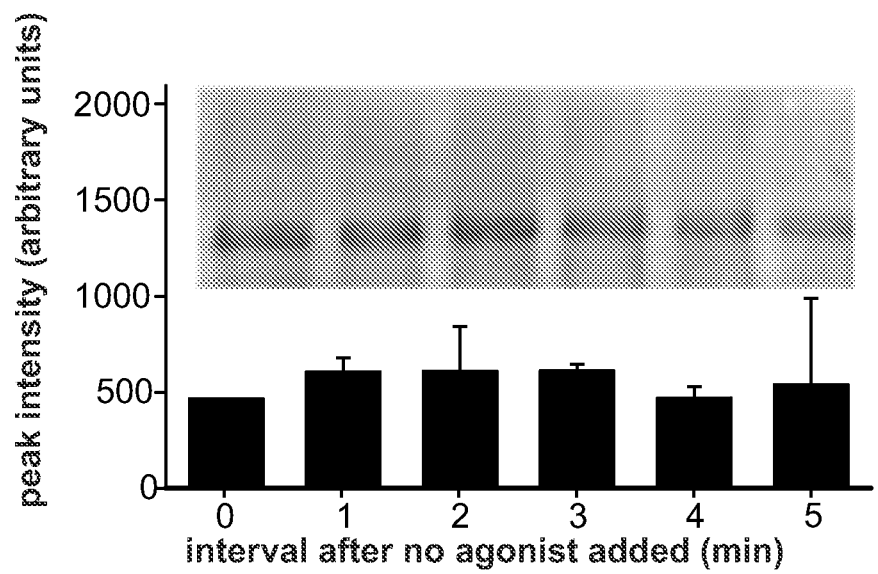

The invention features compositions and methods that are useful for determining platelet reactivity in a biological sample of a subject, identifying subjects that are at increased risk of thrombosis, and selecting appropriate therapies for such high risk subjects.

The invention is based, at least in part, on the discovery that FcγRIIa contributes to (e.g., amplifies) the activation of platelets and thus greater expression of FcγRIIa increases the extent of activation of platelets; that FcγRIIa protein levels per platelet correlate with disease state (e.g., levels of FcγRIIa protein/platelet is two-five fold increased in subjects with atherosclerosis and diabetes, and two-ten fold increased in subjects with end stage renal disease); and that FcγRIIa levels are useful in identifying subjects having an increased propensity to develop thrombotic disease and in selecting appropriate therapies for such subjects. In particular, an increase in platelet reactivity is useful in identifying a subject that could benefit from more aggressive drug treatments (e.g., treatment with a more powerful anti-platelet agent, such as Clopidogrel, Prasugrel, Ticagrelor or Vorapaxar).

Accordingly, the invention provides methods for measuring FcγRIIa because it increases platelet reactivity and as such is a marker of elevated platelet reactivity, including flow cytometry and immunoassay-based methods, diagnostic methods employing FcγRIIa as a marker of platelet reactivity, and methods for selecting an appropriate therapeutic agent for a subject identified as having increased platelet reactivity relative to a reference. Advantageously, the diagnostic methods of the invention can be used on a biological sample (e.g., blood, serum, and plasma) obtained from a subject being treated with an antiplatelet or anticoagulant agent.

In certain embodiments, the invention provides a test device, such as a lateral flow device, that comprises a liquid permeable media that provides for the flow of a liquid sample (e.g., blood, serum, plasma) through the device. Test devices of the invention can be used for the detection of an analyte of interest (FcγRIIa) by a detectably labeled reactant capable of specifically interacting with the analyte (FcγRIIa). The test device described herein is particularly suitable for the detection of an antigen of interest using an antibody that specifically binds the antigen and conventional immunoassay procedures.

FcγRIIa

As reported in more detail below, it was found that when platelet activation induces cytoskeletal rearrangement that FcγRIIa clusters in cytoskeletal lipid rafts. The clustering leads to phosphorylation when FcγRIIa is cross-linked with fibrinogen and coagulation Factor XIII. Phosphorylation of FcγRIIa leads to downstream phosphorylation and ultimately the release of calcium that augments the activation of platelets. Consistent with the association of FcγRIIa with membrane cytoskeletal proteins during activation, results with confocal microscopy and preparations of lipid rafts demonstrated clustering of FcγRIIa confined to membrane cytoskeletal lipid rafts. The results presented herein indicate that rearrangement of membrane cytoskeletal proteins during activation is associated with clustering of FcγRIIa that appears to promote its cross-linking by fibrinogen and Factor XIII. Cross-linking by fibrinogen and Factor XIII leads to phosphorylation by SRC kinases (e.g. Lyn).

Further, fibrinogen and Factor XIII co-immunoprecipitated with FcγRIIa from activated platelets and increased activation of platelets. Inhibition of the binding of fibrinogen to GP IIb-IIIa did not abolish amplification of activation by fibrinogen. Further, platelet activation induced by an activating anti-FcγRIIa antibody was not attenuated by tirofiban. These results indicate that interaction between FcγRIIa and GP IIb-IIIa is sufficient but perhaps not necessary for FcγRIIa to contribute to platelet activation.

Amplification of platelet activation induced by fibrinogen was abolished by IV.3 Fab, an antibody that is a specific inhibitor of FcγRIIa, but not by tirofiban. In contrast, the activation of platelets caused by coagulation Factor XIII was abolished by both IV.3 and tirofiban. Without being bound by any particular theory, this finding is consistent with the hypothesis that the cross-linking of FcγRIIa homodimers with fibrinogen or an anti-FcγRIIa antibody and the cross-linking of heterodimers (FcγRIIa and GP IIb-IIIa) by coagulation Factor XIII leads to phosphorylation of FcγRIIa that amplifies the activation of platelets.

Inhibition of phosphorylation of FcγRIIa appeared to have less effect with higher concentrations of thrombin. This observation is consistent with previous results (Canobbio I, et al., *Cell Signal* 2006; 18:861-70) and indicates that phosphorylation of FcγRIIa is not necessary for activation of platelets. Phosphorylation of FcγRIIa appears to amplify the activation of platelets much in the same way that the release of thromboxane A2 and ADP during the process of activation amplifies the extent of platelet activation (Murray R, et al., *Proc Natl Acad Sci USA* 1989; 86:124-8; and Storey R F, et al., Platelets 2001; 12:443-7). These results are consistent with greater platelet reactivity that has been observed when platelet expression of FcγRIIa is increased (Calverley D C, et al., *Atherosclerosis* 2002; 164:261-7; Canobbio I, et al., *Cell Signal* 2006; 18:861-70; and Serrano F A, et al., *Thromb J* 2007; 5:7).

Coagulation Factor XIII has a powerful effect on the activation of platelets, increasing the extent of activation by nearly 4-fold. These results indicate that the effect of Factor XIII is mediated by FcγRIIa. Furthermore, inhibition of SRC kinase (downstream kinases) by PP2 attenuated activation of platelets. In view of the essential role of Fcγ in GP VI mediated activation, the effect was most profound with convulxin-induced activation.

A clinical phenotype of increased platelet reactivity and evidence of an increased risk of thrombosis was identified when platelet expression of FcγRIIa is increased. Greater platelet expression of FcγRIIa was observed in blood from patients with previous stroke, myocardial infarction, and unstable angina. Somewhat more compelling evidence of a thrombotic phenotype is provided by the association of a greater risk of subsequent thrombotic events in patients with end stage renal disease who have greater platelet expression of FcγRIIa (El-Shahawy M, et. al., *Am J Kidney Dis.* 2007; 49:127-34).

The results disclosed herein demonstrate that activated platelets have phosphorylated FcγRIIa associated with membrane cytoskeletal proteins, fibrinogen, and coagulation Factor XIII. These results indicate that the activation of platelets leads to plasma membrane cytoskeletal rearrangement, the clustering of FcγRIIa, and the cross-linking of FcγRIIa by fibrinogen and Factor XIII in association with lipid raft proteins. Lipid raft proteins (SRC kinases)phosphorylate FcγRIIa that leads to downstream signaling and serves to amplify the activation of platelets.

Based on the results reported herein, it was discovered that increased levels of FcγRIIa on platelets causes and is therefore an indicator of increased platelet reactivity. Moreover, the use of FcγRIIa is superior to other measures of platelet reactivity the level of FcγRIIa is not influenced by commonly used therapies and medicines. Thus, the use of platelet FcγRIIa as a marker of platelet reactivity is not influenced by antiplatelet treatment.

Diagnostics

The present invention features diagnostic assays for the identification of subjects having an increased level of FcγRIIa, which is indicative of high platelet reactivity, and an increased risk of thrombotic disease. In one embodiment, levels of platelet FcγRIIa are measured in a subject sample and used to characterize platelet reactivity in the subject. Any suitable method can be used to detect platelet FcγRIIa in a subject sample and used to characterize platelet reactivity in blood from the subject. Biological samples include bodily fluids (e.g., blood, blood serum, plasma, and saliva). Successful practice of the invention can be achieved with one or a combination of methods that can detect and/or quantify platelet FcγRIIa. Immunoassays in various formats (e.g., flow cytometry, ELISA) are popular methods for detection of analytes captured on a solid phase. Such methods typically involve use of an FcγRIIa—specific antibody.

Virtually any method known in the art can be used to detect FcγRIIa. For example, levels of platelet FcγRIIa are compared by procedures well known in the art, such as flow cytometry, immunoassay, ELISA, western blotting, radio-immunoassay, immunocytochemistry, binding to magnetic and/or antibody-coated beads, in situ hybridization, fluorescence in situ hybridization (FISH), flow chamber adhesion assay, microarray analysis, or colorimetric assays. Methods may further include, one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^a$, atmospheric pressure photoionization mass spectrometry (APPI-MS), APPI-MS/MS, and APPI-(MS)$_a$, quadrupole mass spectrometry, fourier transform mass spectrometry (FTMS), and ion trap mass spectrometry, where n is an integer greater than zero.

Detection methods may include use of a biochip array. Biochip arrays useful in the invention include protein and polynucleotide arrays. One or more markers are captured on the biochip array and subjected to analysis to detect the level of the markers in a sample.

Platelet FcγRIIa may be captured with capture reagents fixed to a solid support, such as a biochip, a multiwell microtiter plate, a resin, or a nitrocellulose membrane that is subsequently probed for the presence or level of a marker. Capture can be on a chromatographic surface or a biospecific surface. For example, a sample containing the markers, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry).

Optical methods include microscopy (both confocal and non-confocal), imaging methods and non-imaging methods. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present invention comprise performing quantitative MS to measure the serum peptide marker. The method may be performed in an automated (Villanueva, et al., *Nature Protocols* (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

The protein fragments, whether they are peptides derived from the main chain of the protein or are residues of a side-chain, are collected on the collection layer. They may then be analyzed by a spectroscopic method based on matrix-assisted laser desorption/ionization (MALDI) or electrospray ionization (ESI). The preferred procedure is MALDI with time of flight (TOF) analysis, known as MALDI-TOF MS. This involves forming a matrix on the membrane, e.g. as described in the literature, with an agent which absorbs the incident light strongly at the particular wavelength employed. The sample is excited by UV, or IR laser light into the vapour phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are commercially available from PerSeptive Biosystems, Inc. (Frazingham, Mass., USA) and are described in the literature, e.g. M. Kussmann and P. Roepstorff, cited above.

In other embodiments, levels of FcγRIIa are detected in combination with one or more additional markers. While individual markers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, methods of the present invention provide for the measurement of more than one marker or clinical parameter.

The use of multiple markers increases the predictive value of the test and provides greater utility in diagnosis, toxicology, patient stratification and patient monitoring. The process called "Pattern recognition" detects the patterns formed by multiple markers. The inclusion of additional markers may improve the sensitivity and specificity in determining a patient's risk for developing a thrombotic disease or disorder associated with an undesirable increase in platelet reactivity. Subtle variations in data from clinical samples indicate that certain patterns of protein level or expression (e.g., FcγRIIa level) can predict phenotypes such as an increase in platelet reactivity, or can identify a patient that could benefit from more aggressive drug treatments (e.g., treatment with a more powerful anti-platelet agent, such as Clopidogrel, Prasugrel, Ticagrelor, or Vorapaxar).

Expression levels of platelet FcγRIIa are correlated with platelet reactivity, and thus are useful in diagnosis. Antibodies that specifically bind FcγRIIa, or any other method known in the art may be used to monitor expression of platelet FcγRIIa. Detection of an alteration relative to a normal, reference sample can be used as a diagnostic indicator of platelet reactivity. In particular embodiments, a 2, 3, 4, 5, or 6-fold change in the level of platelet FcγRIIa is indicative of platelet reactivity.

In one embodiment, the level of platelet FcγRIIa is measured on at least two different occasions and an alteration in the levels as compared to normal reference levels over time is used as an indicator of platelet reactivity or the propensity to develop thrombosis. In general, levels of platelet FcγRIIa are present at low levels (about 6,000 copies per platelet) in a healthy subject (i.e., those who do not have reactive platelets). In one embodiment an increased level of platelet FcγRIIa (from about 8,000 to 20,000 or 10,000 to 20,000 copies per platelet) is indicative of platelet reactivity. In another embodiment the increased level is from about 8,000 to 15,000 or 12,000 to 15,000 copies per platelet. Preferably, FcγRIIa copy/platelet is measured using FACS analysis.

The diagnostic methods described herein can be used individually or in combination with any other diagnostic method described herein for a more accurate diagnosis of the presence or severity of thrombotic disease.

The correlation may take into account the amount of platelet FcγRIIa in the sample compared to a control amount of platelet FcγRIIa (e.g., in normal subjects or in subjects where platelet reactivity is undetected). A control can be, e.g., the average or median amount of platelet FcγRIIa present in comparable samples of normal subjects. The control amount is measured under the same or substantially similar experimental conditions as in measuring the test amount. As a result, the control can be employed as a reference standard, where the normal phenotype is known, and each result can be compared to that standard, rather than re-running a control.

Accordingly, a marker profile may be obtained from a subject sample and compared to a reference value obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate determination of cancer status.

In certain embodiments, the methods further comprise selecting anti-thrombotic therapy. For example, where a 2-5 fold, 5-10 fold, or 10-25 fold increase in platelet reactivity relative to a reference identifies a patient that could benefit from more aggressive drug treatments (e.g., treatment with a more powerful anti-platelet agent, such as Clopidogrel, Prasugrel, Ticagrelor, or Vorapaxar). The invention also provides for such methods where platelet FcγRIIa is measured again after anti-thrombotic therapy. In these cases, the methods are used to monitor the status of the platelet reactivity.

Antibodies

As reported herein, antibodies that specifically bind FcγRIIa are useful in diagnostic, as well as therapeutic methods. For example, antibodies that act as platelet FcγRIIa antagonists (e.g., IV.3 Fab) are particularly useful in the methods of the invention. In particular embodiments, the invention provides methods of using anti-platelet FcγRIIa antibodies for the inhibition of platelet reactivity. IV.3 is a monoclonal anti-FcγRIIa antibody that inhibits the phosphorylation of platelet FcγRIIa during platelet activation.

Other antibodies useful in the invention are those that attenuate platelet FcγRIIa signaling. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of an intact antibody, clear more rapidly from the circulation, and may have less non-specific tissue binding than an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anticarcinoembryonic antigen (CEA)diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv)diners is described by Gruber et al. (J. Immunol. 152:5368, 1994). Trispecific antibodies are described by Tutt et al. (J. Immunol. 147:60, 1991).

Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In one embodiment, an antibody that binds platelet FcγRIIa is monoclonal. Alternatively, the anti-platelet FcγRIIa antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')2" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing soluble polypeptides, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding human FcγRIIa or immunogenic fragments thereof, can be provided to the host in a delivery vehicle that is taken up by immune cells of the host. The cells will in turn express the human FcγRIIa thereby generating an immunogenic response in the host. Alternatively, nucleic acid sequences encoding human FcγRIIa or immunogenic fragments thereof, can be expressed in cells in vitro, followed by isolation of the human FcγRIIa and administration of the FcγRIIa to a suitable host in which antibodies are raised.

Alternatively, antibodies against platelet FcγRIIa may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Inhibitory Nucleic Acids

Inhibitory nucleic acid molecules are those oligonucleotides that inhibit the expression or activity of platelet FcγRIIa for the prevention of thrombosis and the treatment of thrombosis-related disorders. Such oligonucleotides include single and double stranded nucleic acid molecules (e.g., DNA, RNA, and analogs thereof) that bind a nucleic acid molecule that encodes FcγRIIa (e.g., antisense molecules, siRNA, shRNA) as well as nucleic acid molecules that bind directly to a platelet FcγRIIa polypeptide to modulate its biological activity (e.g., aptamers).

Ribozymes

Catalytic RNA molecules or ribozymes that target an antisense FcγRIIa sequence of the present invention can be used to inhibit expression of a FcγRIIa nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference. Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an sirNA approach in mammals was demonstrated in vivo by McCaffrey et al. (Nature 418: 38-39.2002). Given the sequence of a target gene, siRNAs may be designed to inactivate that gene. Such siRNAs, for example, could be administered directly to an affected tissue, or administered systemically. The nucleic acid sequence of an Parl gene can be used to design small interfering RNAs (siRNAs). The 21 to 25 nucleotide siRNAs may be used, for example, as therapeutics to treat lupus.

The inhibitory nucleic acid molecules of the present invention may be employed as double-stranded RNAs for RNA interference (RNAi)-mediated knock-down of platelet FcγRIIa expression. In one embodiment, platelet FcγRIIa expression is reduced in megakaryocytes. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Delivery of Nucleobase Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Design of a Test Device

The test device can take any form desired that provides for the flow of a liquid test sample from the point of contact with the test sample past the test and/or control sites. In general, the test device of the present invention includes an interior flow pathway that includes one or more liquid permeable materials. In a first portion, the device includes a site for the application of a liquid sample. This first portion of the device also includes an analyte-binding conjugate, such as an antibody that specifically binds an antigen of interest (e.g., FcγRIIa, platelet surface proteins). The analyte binding conjugate typically binds the analyte to form a complex. Complex formation (e.g., formation of an antigen/antibody conjugate complex) may occur at any point in the interior flow pathway after the analyte contacts the analyte-binding conjugate. For example, complex formation may occur or continue as the sample flows from the first portion to the second portion of the device.

The second portion of the device has a variety of features that enhance functionality. In one embodiment, the second portion is composed of a material capable of filtering the sample to prevent the flow of particulate matter through the device. In another embodiment, the second portion facilitates complex formation by increasing the time required for the liquid to flow from the site of application to the test site. Accordingly, the dimensions of the second portion may be altered (e.g., increased or decreased) to empirically determine for each application those dimensions that enhance sensitivity while reducing false positives, i.e., optimizing the signal-to-noise ratio. In yet another embodiment, the second portion of the device can be used to deliver a desired agent to the liquid as it flows through the device. For example, the second portion may be impregnated with a buffer (e.g., TRIS (tris(hydroxymethyl) aminomethane), sodium carbonate), surfactant (e.g., Tween® (polysorbate), Triton™ (2-[4-(2,4,4-trimethylpentan-2-yl) phenoxylethanol)), preservative (e.g., Na azide, thimerosol), salt, or other agent, such that contact of the sample with the second portion of the device alters the sample. Exemplary alterations include an increase or decrease in the pH of the sample, in the salt concentration, in the buffering capacity, or in the binding between the conjugate and the analyte.

The third portion of the device includes a test site, which acts as a readout zone that provides for detection of an analyte in the sample. Various means for detecting the presence of an analyte at a test site are known in the art. In a competitive assay, a labeled probe competes with an analyte of interest for binding to a detector at the test site. The more analyte that is present in the sample, the more effectively it will be able to compete with, and/or displace, the binding of a detector. The hallmark of most competitive assays is that an increase in the amount of analyte in the sample results in a decrease of signal in the readout zone. In contrast, a "sandwich" format typically involves mixing the test sample with a detection probe conjugated with a specific binding member (e.g., antibody). In this embodiment, the conjugate and the analyte bind to form a complex. These complexes are then allowed to contact a receptive material (e.g., antibody) that is immobilized at the test site. The analyte/conjugate complex binds to the immobilized receptive material to form a "sandwich complex" (e.g., antibody conjugate/antigen/antibody). In this approach, detection of the "sandwich complex" indicates the presence of analyte in the sample.

It may be desirable to include a positive control to indicate that the liquid sample has traversed the interior flow path from the site of application past the test site. In a competitive assay format, the first portion of the device further includes a control conjugate and the third portion of the device includes a control site with a receptive material that binds the control conjugate. The control site is situated in the third portion of the device downstream from the test site. Detection of control conjugate binding at the control site indicates that the liquid sample flowed from the application site past the test site to the control site. In a sandwich assay format, a control antibody that binds the anti-antigen antibody is fixed at the control site. In the presence or absence of an antigen, excess anti-antigen antibody is detected at the control site.

The device may also include in a fourth portion a wicking pad that contains sorbent material capable of absorbing or adsorbing excess liquid present in the liquid sample.

In one embodiment, the test device contains a liquid permeable material defining the following portions in capillary communication:

a) a first portion that is the site for application of a liquid sample, comprising a liquid permeable medium, an anti-antigen antibody conjugate and a control antibody conjugate, where the first portion is between 5 mm and 20 mm in length; for example, the length of the first portion is equal to any integer between 5 and 20 (5, 10, 15, 20 mm in length);

b) a second portion comprising a liquid permeable medium, where the second portion overlaps the first portion by at least 1, 2, 3, 4, or 5 mm; and the length of the second portion is between 10 mm and 40 mm; for example, the length of the second portion is any integer between and 40 (e.g., 10, 15, 20, 25, 30, 35, 40); and c) a third portion that is the site for detecting the binding of the anti-antigen antibody conjugate at a test site and the binding of the control antibody conjugate at a control site, the third portion comprising a liquid permeable medium having the antigen fixed to the medium at the test site, and having an antibody that binds the control antibody present at a control site, wherein the third portion is between 15 and 40 mm in length; for example, is any integer between 15 and 40 (e.g., 15, 20, 25, 30, 35, 40); and the second portion overlaps the third portion by at least 1, 2, 3, 4, or 5 mm.

In a fourth portion the device contains sorbent material. The sorbent material has a length between 25 and 75 mm.

For example, the length is an integer between 25 and 75 (e.g., 25, 35, 50, 60, 70, 75). In one embodiment, the fourth portion overlaps the third portion by at least 1, 2, 3, 4, or 5 mm.

In general the interior flow path is between 1 mm and 10 mm in width; for example, the width of a test device (e.g., test strip) is any integer between 1 and 10 (e.g., 1, 2, 3, 4, 5, 6, 7, 8, 9, 10). In one embodiment the width of the strip is 3.8 mm. Desirably, a test device of the invention has increased sensitivity relative to a conventional test device. Sensitivity of a test device of the invention is increased by at least 5%, 10%, 25%, 50%, 75%, 100%, 150%, or 200% relative to a conventional test device.

As described herein, the test device includes a conjugate that binds an analyte. In one approach, the conjugate is an antibody capable of binding FcγRIIa, either alone or when conjugated to another compound. Any antibody, antibody conjugate, or fragment thereof that binds an antigen of interest may be used in the present invention. Such antibodies or antibody conjugates are present within the interior flow path of the test device. Suitable antibodies include, but are not limited to, polyclonal antibodies, monoclonal antibodies, or fragments thereof.

In order to detect the antibody/antigen complex within the test device, a detector reagent, or conjugate, must be coupled to the antibody or antigen. Exemplary conjugates include colored reagents, fluorescent compounds, enzymes, and radioactive isotopes. Colored or fluorescent compounds include gold particles, colored or fluorescent latex particles, polystyrene beads, and dyes, such as fluorescein isothiocyanate, BODIPY FL, Oregon Green, Alexa Fluor 488, phycoerythrin and phycocyanin. Colloidal metals, metal sols and other types of colored particles useful as marker substances in immunoassay procedures are known in the art. See, for example, U.S. Pat. No. 4,313,734. Antibody conjugates are widely available, for example, from a variety of well-known commercial sources (e.g., Molecular Probes (e.g., Zenon® labeling technology), Nanoprobes (e.g., Nanogold® Gold-Antibody Conjugates).

Enzymes that may be coupled to an antibody include peroxidases (such as horseradish peroxidase), phosphatases (such as acid or alkaline phosphatase), ß-galactosidase, urease, glucose oxidase, carbonic anhydrase, acetylcholinesterase, glucoamylase, lysozyme, malate dehydrogenase, glucose-6-phosphate dehydrogenase, ß-glucosidase, proteases, pyruvate decarboxylase, esterases, luciferase, or any other enzyme known to the skilled artisan. Enzymes are not in themselves detectable but must be combined with a substrate to catalyse a reaction the end product of which is detectable.

Antibodies, antibody conjugates, protein-antigen conjugates, and protein-hapten conjugates are fixed within the interior flow path using standard methods known to the skilled artisan. Protein immobilization protocols are known to the skilled artisan. See, for example, Laboratory Techniques in Biochemistry and Molecular Biology, Tijssen, Vol. 15, Practice and Theory of Enzyme Immunoassays, Chapter 13, The Immobilization of Immunoreactants on Solid Phases, pp. 297-328, and the references cited therein. In one approach, an antibody is immobilized directly on a solid support by physical adsorption or is bound covalently or through bridging molecules such as protein A, polylysine or to a solid support.

Interior Flow Path

The test device comprises an interior flow path that facilitates the flow of a liquid sample through the device. This interior flow path contains one or more liquid permeable materials or membranes composed of any relatively inert material or a combination of materials suitable for transporting a liquid (e.g., glass fibers, polyester, nitrocellulose, fibers of cellulose or derivatives thereof, non-cellulose hydrocarbon materials, ceramics) from the contact site past the test and/or control sites and, optionally, into a reservoir. Suitable materials for use in the interior flow path are wettable and exhibit low non-specific binding. Materials having increased sorptivity promote the flow of liquid. Different materials having different absorption characteristics or sorptivities may be used in various portions of the flow path. If desired, the materials to be used are screened for optimal pore size and density in order to facilitate the controlled distribution of an antibody within a membrane, to optimize reaction kinetics, or to optimize the sensitivity, discriminatory ability, or signal-to-noise ratio of the device.

Solid Supports

For most applications, the test device includes an interior flow pathway fixed to a solid support. The physical shape of the solid support is not critical, although some shapes may be more convenient than others for the present purpose. Accordingly, the solid support may be in the shape of a paper strip, dipstick, membrane (e.g. a nylon membrane or a cellulose filter), a plate (e.g. a microtiter plate) or solid particles (e.g. latex beads). The solid support may be made of any suitable material, including but not limited to a plastic (e.g., polyethylene, polypropylene, polystyrene, latex, polyvinylchloride, polyurethane, polyacrylamide, polyvinylalcohol, nylon, polyvinyl acetate, or any suitable copolymers thereof), cellulose (e.g. various types of paper, such as nitrocellulose paper and the like), a silicon polymer (e.g. siloxane), a polysaccharide (e.g. agarose or dextran), or an ion exchange resin (e.g. conventional anion or cation exchange resins).

Sorbent Reservoir

The test device optionally includes a fourth portion that forms a reservoir of adsorbent or absorbent material. This reservoir sorbs excess liquid as it flows through the test device. For some applications, such as where the concentration of antigen in a test sample is particularly low, it may be desirable to apply large volumes of a liquid test sample to the test device. In such cases, the presence of the adsorbent material may enhance the sensitivity of antigen detection. Optionally, the region of the flow path in the test cell defining the test and control sites is restricted in cross-sectional area relative to other regions of the flow path. This feature produces a "bottle-neck" effect wherein the antigen in the entire volume of adsorbed sample must pass through an area of restricted flow immediately above the test site. This "bottle-neck" may facilitate sandwich formation. Suitable sorbent materials include virtually any commercial material (e.g., synthetic or natural materials, such as cotton) capable of absorbing many times its weight in water. Such materials are widely available in commerce.

Methods of Using the Test Device

The invention provides methods of using a test device of the invention for the detection of an analyte (e.g., an antigen) in a test sample. In one example, the assay is conducted by placing the leading edge (first portion) of a lateral flow device in contact with a liquid test sample. In another example, the sample is brought into contact with the device by applying a liquid test sample to the first portion of the lateral flow device in a drop-wise fashion.

Test Samples

Methods and compositions of the invention are useful for the identification of an analyte (FcγRIIa) in a test sample. In one embodiment, the methods of the invention are suitable for detecting analytes of biological origin. Test samples include, but are not limited to, any liquid containing a dissolved or dispersed analyte (FcγRIIa) of biological origin. Exemplary test samples include body fluids (e.g. blood, plasma, amniotic fluid, sputum, urine, cerebrospinal fluid, lymph, tear fluid, feces, or gastric fluid), tissue extracts, or any liquid or biologic fluid containing a platelet. Exemplary conjugates that specifically bind platelets include without limitation antibodies to glycoprotein (GP) IIb (e.g., anti-CD41 or CD41a; antibodies to GP IIIa (e.g., anti-CD61); antibodies to GP V (e.g., anti-CD42d); antibodies to GP Ib (e.g., anti-CD42b); antibodies to GP IX such as anti-CD42a; antibodies to lysosomal membrane proteins (e.g., anti-CD63); antibodies to PECAM (e.g., anti-CD31). In various embodiments, a test device of the invention detects a FcγRIIa peptide or protein (e.g., on a platelet). If the test sample is not in itself sufficiently fluid for the present purpose, it may be admixed with a suitable fluid to the desired fluidity, for instance by homogenization.

Kits

In another aspect, the invention provides kits for aiding in assessing platelet reactivity (e.g., determining a level of FcγRIIa expressed on platelets in a sample, identifying a subject having thrombosis or at risk of having thrombosis, selecting a treatment method for a subject having thrombosis or at risk of having thrombosis, and the like), which kits are used to detect biomarkers according to the invention. In one embodiment, the kit comprises agents that specifically recognize FcγRIIa. In specific embodiments, the agents are antibodies. Fluorescently labeled antibodies level are useful when flow cytometry methods are used to determine the level of FcγRIIa expressed on platelets in a sample. In a further embodiment, such a kit can comprise instructions for use in any of the methods described herein. In various embodiments, the instructions provide suitable operational parameters in the form of a label or separate insert. For example, the instructions may inform a consumer about how to collect the sample, how to wash the probe or the particular biomarkers to be detected, or how to determine platelet reactivity based on a measurement the level of FcγRIIa. In yet other embodiments, the kit can comprise one or more containers with controls (e.g., biomarker samples) to be used as standard(s) for calibration. In still other embodiments, the kit can comprise one or more therapeutic agents for the treatment of thrombosis (e.g., ADP receptor antagonists, PAR antagonists, and the like).

In additional embodiments, the invention provides kits that include a test device for the detection of an analyte in a sample. In one embodiment, the kit includes a lateral flow device described herein. In some embodiments, the kit comprises a container, which contains the lateral flow device; such containers can be boxes, ampoules, bottles, vials, tubes, bags, pouches, blister packs, or other suitable container forms known in the art. In one embodiment, such containers may be sterile. Such containers can be made of plastic, glass, laminated paper, metal foil, or other materials suitable for holding medicaments.

If desired the device is provided together with instructions for using it to identify the presence or absence of FcγRIIa in a sample. The instructions will generally include information about the use of the device for the identification of a particular analyte, such as FcγRIIa. The instructions may be printed directly on the container (when present), or as a label applied to the container, or as a separate sheet, pamphlet, card, or folder supplied in or with the container. If desired, the kit may also include a standard measure pipet, a test vial, and/or a liquid (e.g., ethanol, methanol, organic solvent, suitable buffer, such as phosphate buffered saline, or water) to be used in the extraction of a sample.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: FcγRIIa is Phosphorylated Following Platelet Activation

Figure 2A:
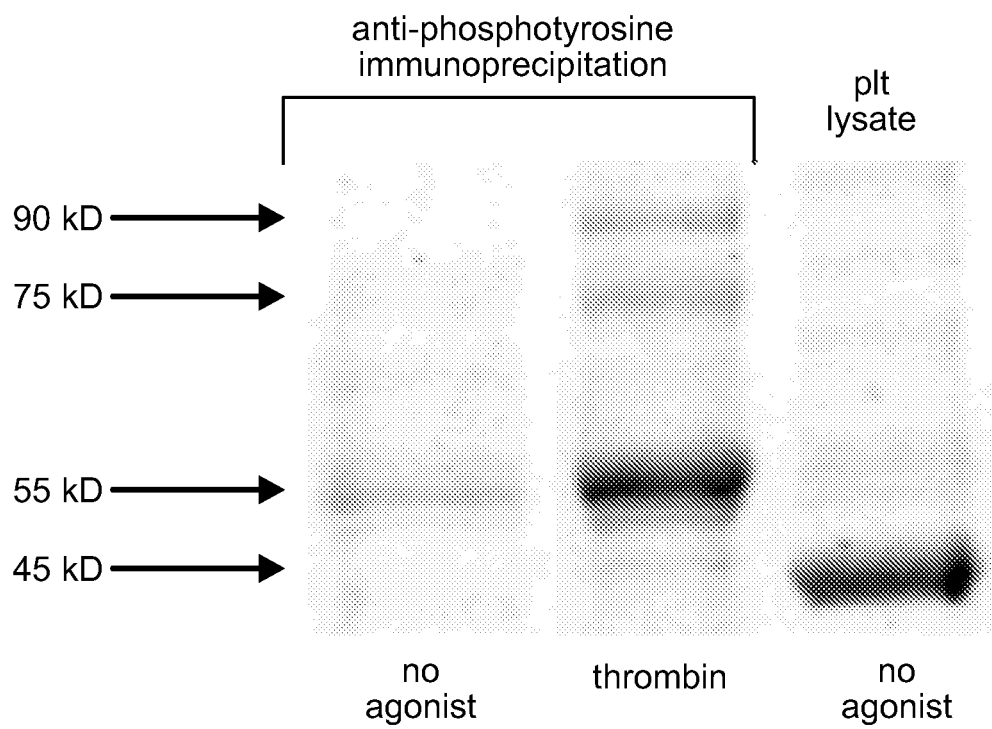
FIGS. 2A and 2B are a western blot and a gel.

Phosphorylation of immunoprecipitated FcγRIIa following activation with thrombin, convulxin, ADP, and PAF was quantified from platelets isolated from healthy subjects (FIGS. 1A-1E). Although a band corresponding to the expected molecular weight of FcγRIIa was apparent at 45 kDa, additional bands at 55 kDa, 75 kDa, and 90 kDa demonstrated phosphorylation. In subsequent experiments, immunoprecipitation was performed with the use of an anti-phosphotyrosine antibody (4G10). These gels confirmed that phophorylated FcγRIIa was associated with each of the 4 bands originally identified (FIG. 2A). Phosphorylation of FcγRIIa was greatest early (1-2 min) after exposure to thrombin, convulxin, and PAF whereas maximal effects of ADP were not apparent until later (3-5 min).

Mass spectrometry was used to identify proteins or fragments of proteins that coimmunoprecipitated with FcγRIIa after activation of platelets. As expected, approximately 45% of the protein content of the band at 55 kDa was IgG (used for the immunoprecipitation). Fibrinogen (predominantly β chain, 33%), actin (3%) and the SRC kinase Lyn (1%) were the proteins co-immunoprecipitated in the 55 kDa band. Without being bound to a particular theory, modest phosphorylation of FcγRIIa is associated with substantial phosphorylation of Lyn. Proteins comprising the 75 kDa band included coagulation Factors XIII (A subunit, 38%) and V (4%), fibrinogen (α,β, and γ chains 24%), nexilin (3%), actin (1%) and myosin (1%). Proteins comprising the 90 kDa band included fibrinogen (γ chain, 80%), gelsolin (6%), filamin (1%), and coagulation Factor XIII (1%). Accordingly, with activation of platelets FcγRIIa was associated predominantly with fibrinogen, coagulation Factor XIII, and constituents of the platelet cytoskeleton (actin, myosin, nexilin, gelsolin, and filamin).

Example 2: FcγRIIa Co-Localizes with Lipid Rafts with Platelet Activation

Figure 2B:
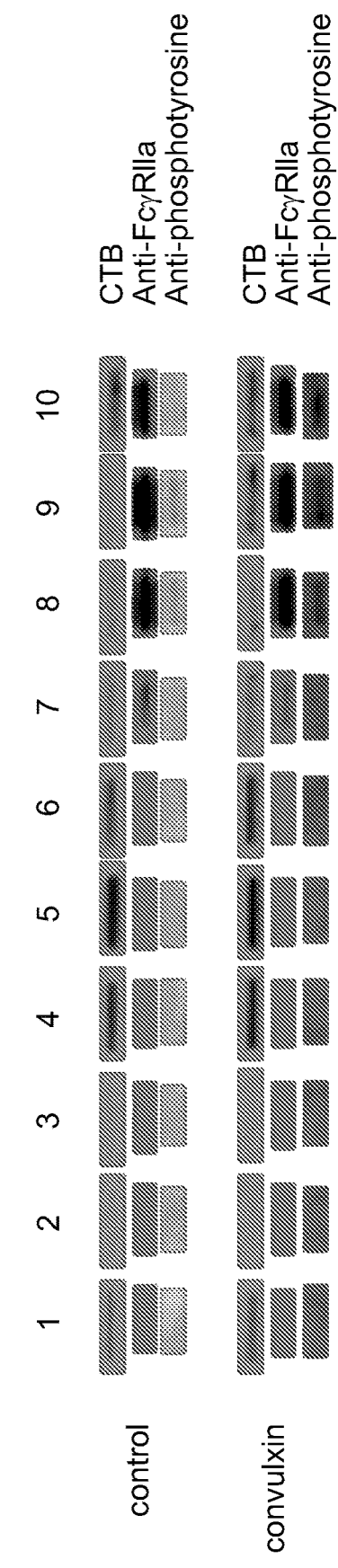

Lipid rafts were isolated and extracts from platelets that had not been activated demonstrated FcγRIIa in fractions 8-10, the membrane cytoskeleton (FIG. 2B). After activation, FcγRIIa remained associated with the membrane cytoskeleton (fractions 8-10), phosphorylation of FcγRIIa was seen in fractions 8-10, and plasma membrane lipid rafts were seen in fractions 9 and 10 (FIG. 2B). FcγRIIa was not seen in association with soluble lipid rafts (fractions 4-6).

Figure 3:
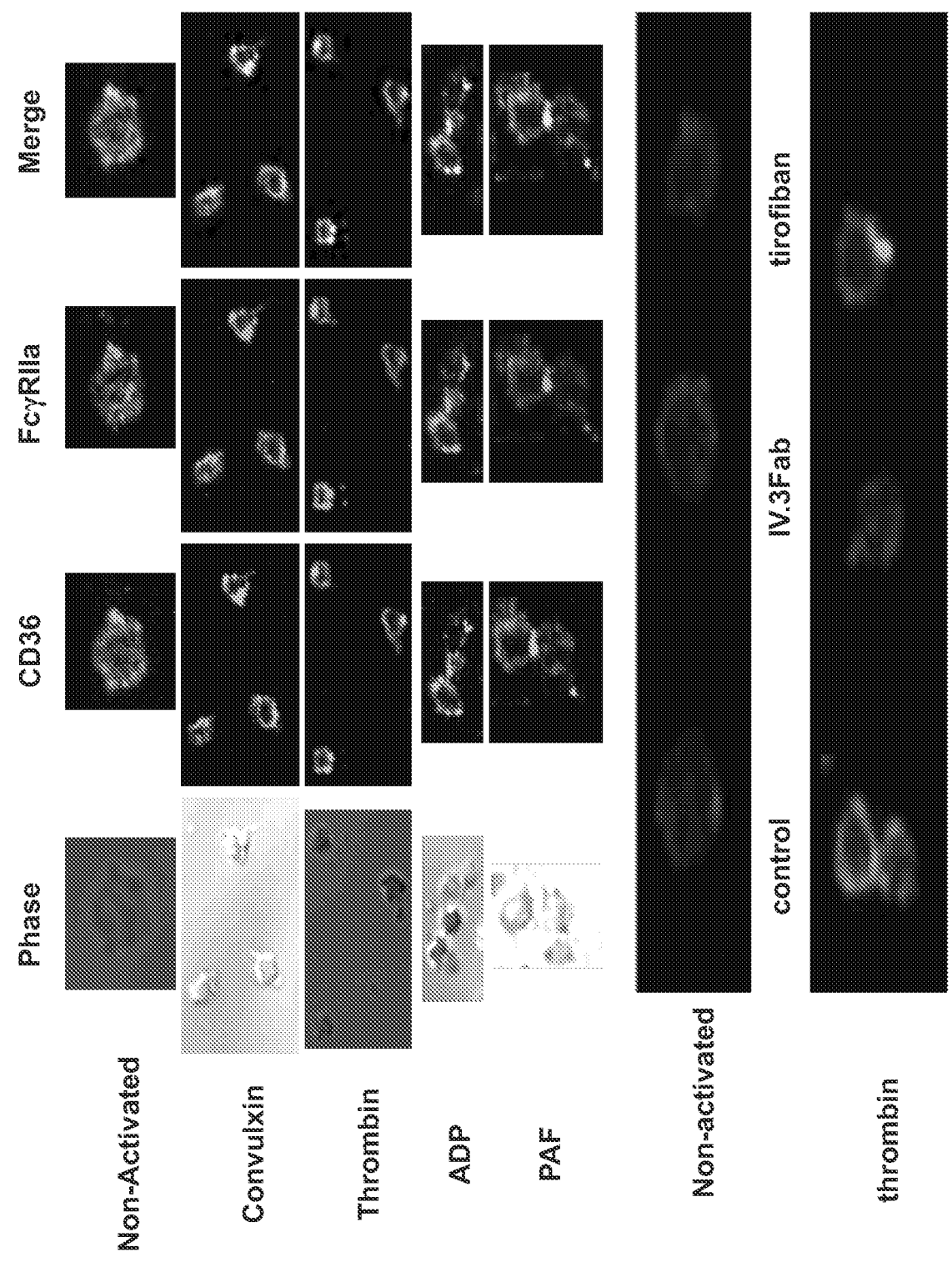
FIG. 3 is a set of photomicrographs showing the subcellular localization of CD36 and FcγRIIa before and during platelet activation. Expression of FcγRIIa and CD36 by human platelets (top panel). PRP was prepared, and platelets were activated with thrombin (50 nM), convulxin (10 ng/ml), ADP (25 µM), and PAF (100 nM). After fixation with Optilyse (1.5% formaldehyde), platelets were pretreated with 1% BSA before incubation with a mouse anti-CD36 and a goat anti-FcγRIIa for 1 hr. After 3 washes in HT buffer, secondary antibodies were used to identify CD36 (Alexa 488 anti-mouse IgG) and FcγRIIa (Alexa 555 anti-goat IgG). Platelets were imaged with the use of a Zeiss LSM 510 META confocal/scanning laser microscope. For each condition, representative platelets on the right were imaged with differential interference contrast (phase contrast). Fluorescence imaging was used to identify CD36 (green signal) and FcγRIIa (red signal). Colocalization is identified by a yellow signal. Activation of platelets was associated with colocalization of lipid rafts and FcγRIIa. The effect of an antagonist of FcγRIIa (Fab fragment of IV.3) and an antagonist of GP IIb-IIIc (tirofiban) on the platelet expression of FcγRIIa (bottom panel). Non-activated platelets and thrombin-activated platelets were pretreated with IV.3 (100 µg/ml) or tirofiban (0.5 µg/ml). Representative platelets exhibited reduction in the clustering of FcγRIIa by pretreatment with IV.3. Magnification is 2,000×.

Confocal microscopy demonstrated a homogeneous surface expression of FcγRIIa in the absence of activation and clustering of FcγRIIa after activation (FIG. 3). Consistent with previous results demonstrating that CD36 is confined to the plasma membrane (Roper K, et al., *Nat Cell Biol* 2000; 2:582-592), nonactivated platelets exhibited a homogeneous surface expression of CD36 and activated platelet exhibited clustering of CD36. Co-localization of lipid rafts with FcγRIIa was greater with activated platelets (FIG. 3).

Figure 4A:
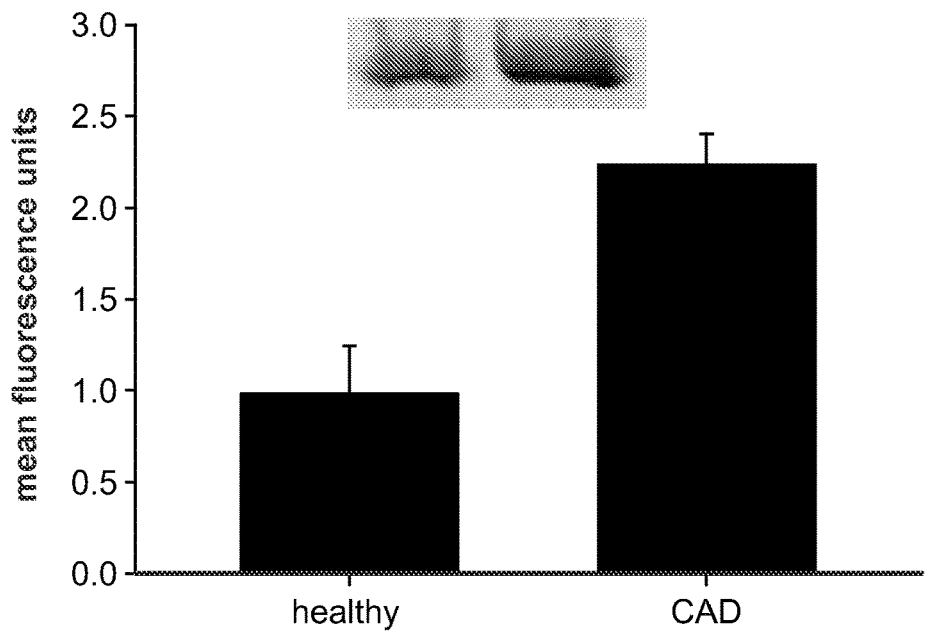
FIGS. 4A and 4B are graphs and western blots showing the expression of FcγRIIa (FIG. 4A) and the phosphorylation of FcγRIIa (FIG. 4B) in response to thrombin. Patients with previous myocardial infarction or coronary revascularization who were taking aspirin, but no other antiplatelet or anticoagulant agent, were screened to identify 3 patients who had elevated expression of FcγRIIa (mean fluorescence intensity >2). Platelet expression of FcγRIIa in healthy subjects was found to be less than 1.5 units (n=5). To confirm results obtained with the use of flow cytometry, Western blot analysis was performed with platelet lysates (FIG. 4A insert). Platelets ($2\times10^8$ in 0.5 ml) isolated with the use of gel filtration were activated with thrombin (50 nM). Phosphorylation of FcγRIIa was quantified as described for FIGS. 1A-1E. Patients in whom expression of FcγRIIa was increased exhibited greater phosphorylation ($p<0.05$) after activation. Results are means±SD.
Figure 4B:
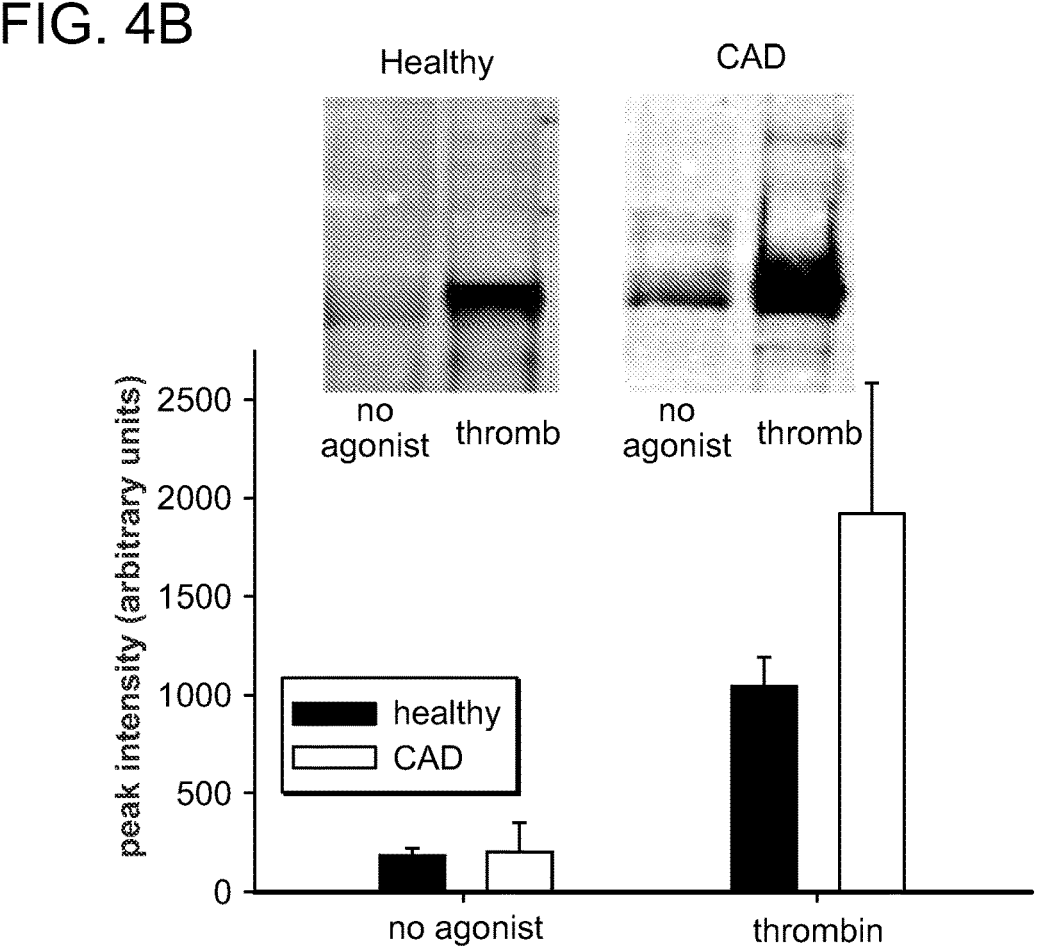

Example 3: Inhibition of FcγRIIa Phosporylation Attenuates Platelet Activation Patients (n=3) with coronary artery disease (CAD) in whom platelet expression of FcγRIIa was 2-fold greater than the average expression by platelets from healthy subjects were chosen for inclusion in this study. Expression of FcγRIIa was identified with the use of flow cytometry and confirmed with Western blot analysis (FIG. 4A). Extracts from platelets with greater expression of FcγRIIa exhibited greater phosphorylation of FcγRIIa (by ~2-fold) after activation with thrombin (FIG. 4B).

Concentrations of IV.3 Fab (100 μg/ml) and the SRC kinase antagonist PP2 (20 μM) that prevented phosphorylation of FcγRIIa during platelet activation were identified. Tirofiban was used to block binding of fibrinogen to GP IIb-IIIa. Goat anti-FcγRIIa cross-links FcγRIIa and was used as a direct acting activator of FcγRIIa.

Figure 5A:
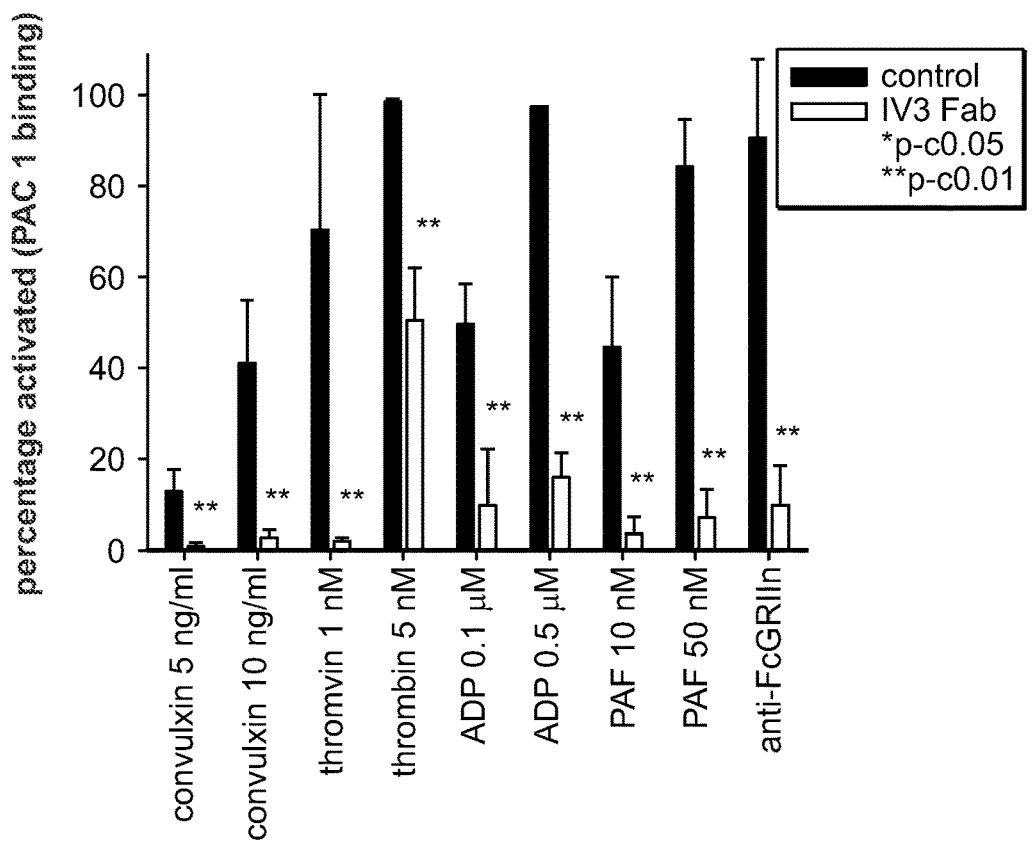
FIGS. 5A-5D are graphs showing the effect of a selective antagonist of FcγRIIa (Fab of IV.3) on the activation and aggregation of platelets. The activation of platelet was assessed with the use of flow cytometry by the binding of PAC-1 (reflecting activation of GP IIb-IIIa, FIG. 5A) or the surface expression of P-selectin (FIG. 5B). Whole blood from healthy subjects (n=6) was added to reaction tubes containing fluorochrome labeled antibodies, selected agonists, and either control conditions or antagonist. Neither equimolar concentrations of non-immune IgG nor the Fab of non-immune IgG attenuated platelet activation (data not shown). IV.3 attenuated activation induced with each agonist, an effect that was most apparent when activation was identified by PAC-1 (FIG. 5A). The aggregation of platelets was assessed with light transmission aggregometry (FIG. 5C). Aggregation that was induced in platelet rich plasma (stirred and warmed to 37° C.) with collagen, thrombin receptor agonist peptide (TRAP), adenosine diphosphate (ADP), and platelet activating factor (PAF) (n=3 for each agonist) was inhibited by IV.3.
Figure 5B:
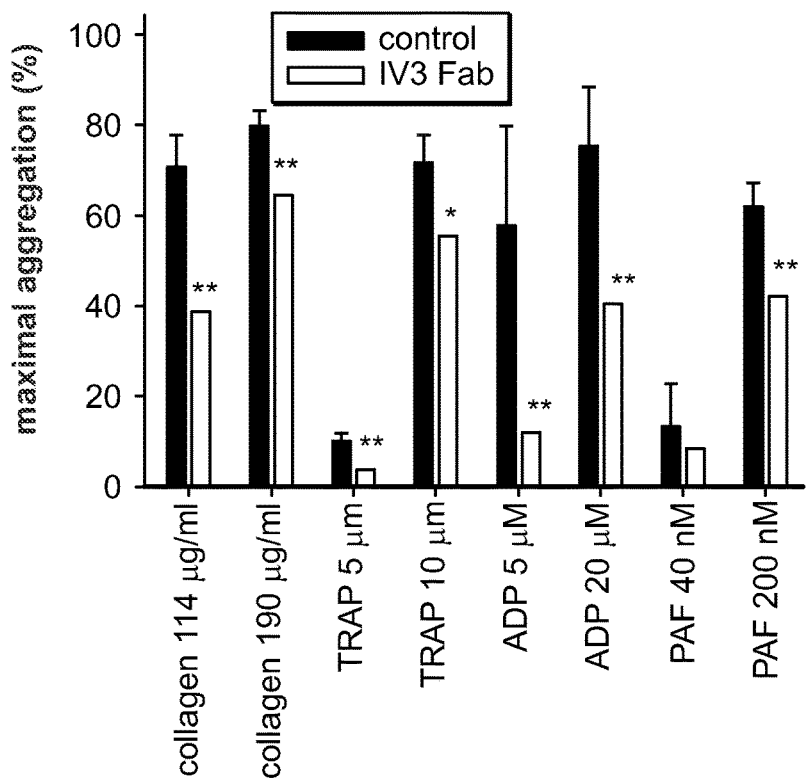
Figure 5C:
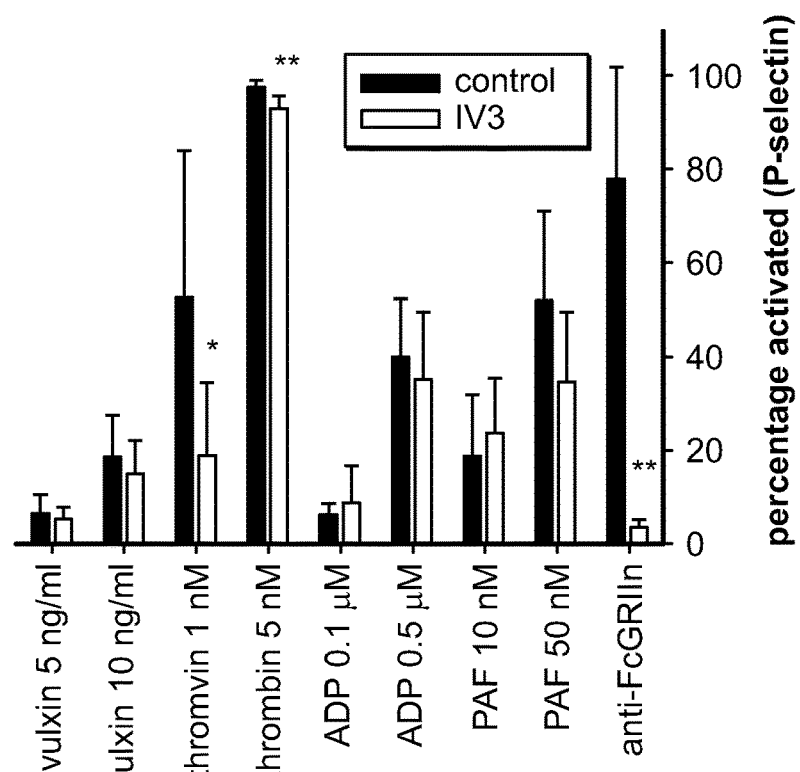
Figure 5D:
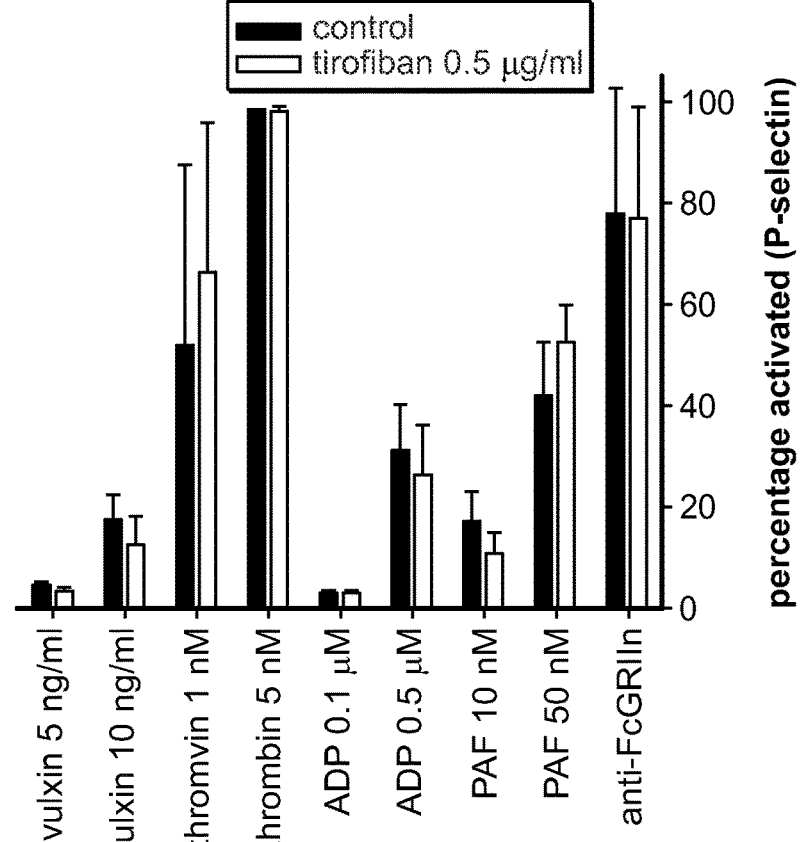
Figures 6A, 6B:
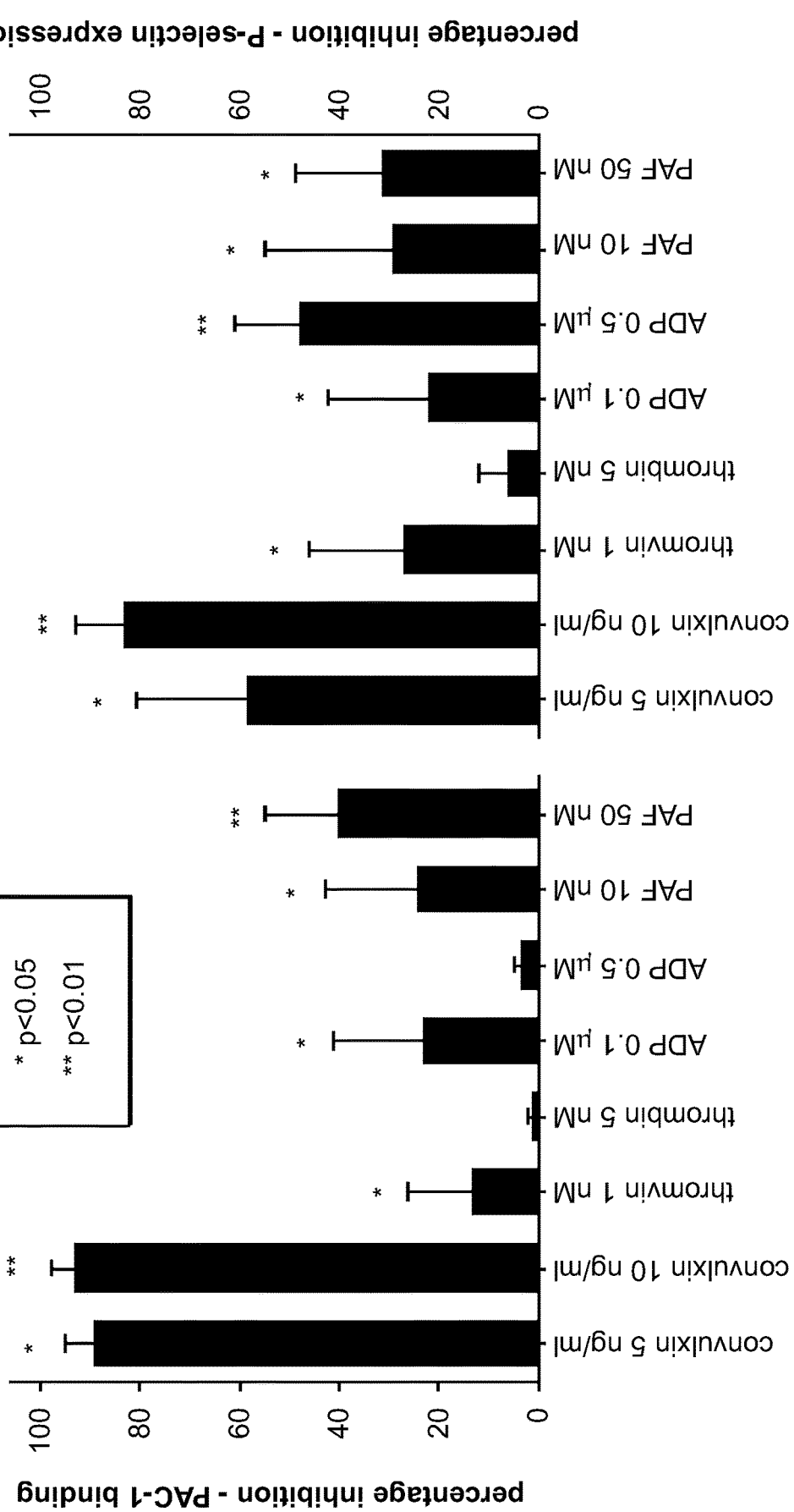
FIGS. 6A and 6B are graphs showing the effect of a non-selective antagonist of SRC kinase (PP2) on the activation of platelets. The activation of platelet was assessed with the use of flow cytometry by the binding of PAC-1 (FIG. 6A) or the surface expression of P-selectin (FIG. 6B). Whole blood from healthy subjects (n=7) was added to reaction tubes containing fluorochrome labeled antibodies, selected agonists, and either control conditions (vehicle alone, dimethyl sulfoxide) or antagonist (PP2, 20 μM). Inhibition of tyrosine phosphorylation by PP2 inhibited activation induced by each agonist. Results are means±SD of the percentage inhibition (1-[PP2/control]). Differences between results with PP2 and control conditions were identified with the use of paired Student's t test.

Inhibition of phosphorylation of FcγRIIa by IV.3 attenuated the activation of platelets, particularly when the activation was identified by the binding of PAC-1 (FIGS. 5A & 5B). Results were confirmed with the use of light transmission aggregometry (FIG. 5C). When thrombin or TRAP was the agonist, the extent of inhibition caused by IV.3 was more apparent when lower concentrations of agonist were used (FIG. 5D). As expected, IV.3 effectively blocked the majority of platelet activation induced by goat anti-FcγRIIa. By contrast, a concentration of tirofiban (0.5 μg/ml) that blocked completely the binding of PAC-1 to platelets did not attenuate the activation of platelets induced by any of the agonists nor did it alter activation induced by goat anti-FcγRIIa. Results with confocal microscopy suggested that IV.3 attenuated clustering of FcγRIIa (FIG. 3). Consistent with the results seen with the specific antagonist IV.3, inhibition of SRC kinases by PP2 attenuated the activation of platelets (FIG. 6).

Purified human fibrinogen was added to whole blood from healthy subjects (to increase the concentration by 500 mg/dl) and the activation of platelets in response to 0.5 μM ADP was assessed by the surface expression of P-selectin. The addition of fibrinogen increased ADPinduced activation of platelets (fold induction—1.5±0.2, n=3). This effect was blocked by pretreatment with IV.3 (100 μg/ml, fold induction—0.9±0.1, $p<0.05$) and appeared to be attenuated by tirofiban (0.5 μg/ml, fold induction—1.2±0.1, $p=0.11$).

Human coagulation Factor XIII was added to blood from healthy subjects (to increase the concentration by 1 μM) and the activation of platelets in response to 0.5 μM ADP was assessed by the surface expression of P-selectin. The addition of Factor XIII increased ADP-induced activation of platelets (fold induction—3.9±0.1, n=3). This effect was blocked by pretreatment with IV.3 (100 μg/ml, fold induction—0.7±0.1, $p<0.001$) and by tirofiban (0.5 μg/ml, fold induction—0.8±0.2, $p<0.001$).

Example 4: FcγRIIa and Platelet Activation in Disease States

Figure 7:
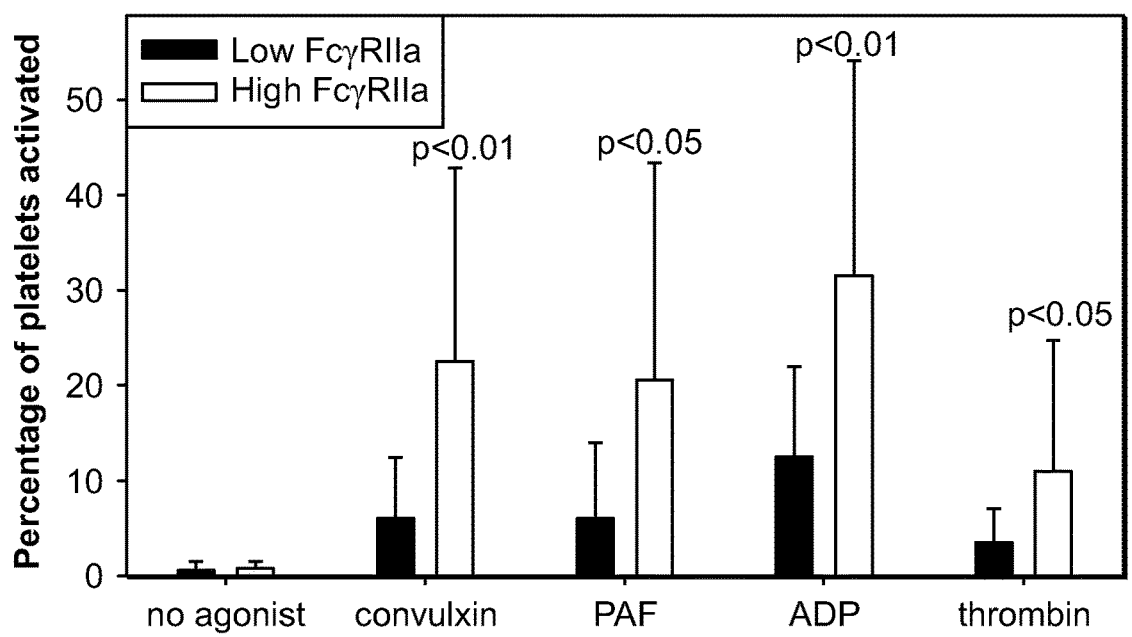
FIG. 7 is a graph showing that the levels of FcγRIIa on the platelets from patients with end stage renal disease (ESRD) correlates with platelet reactivity.

As shown in FIG. 7 platelets derived from patients with end stage renal disease (ESRD) that express high levels of FcγRIIa demonstrated higher percentage of activated platelets than platelets that express lower levels of FcγRIIa.

Figure 8A:
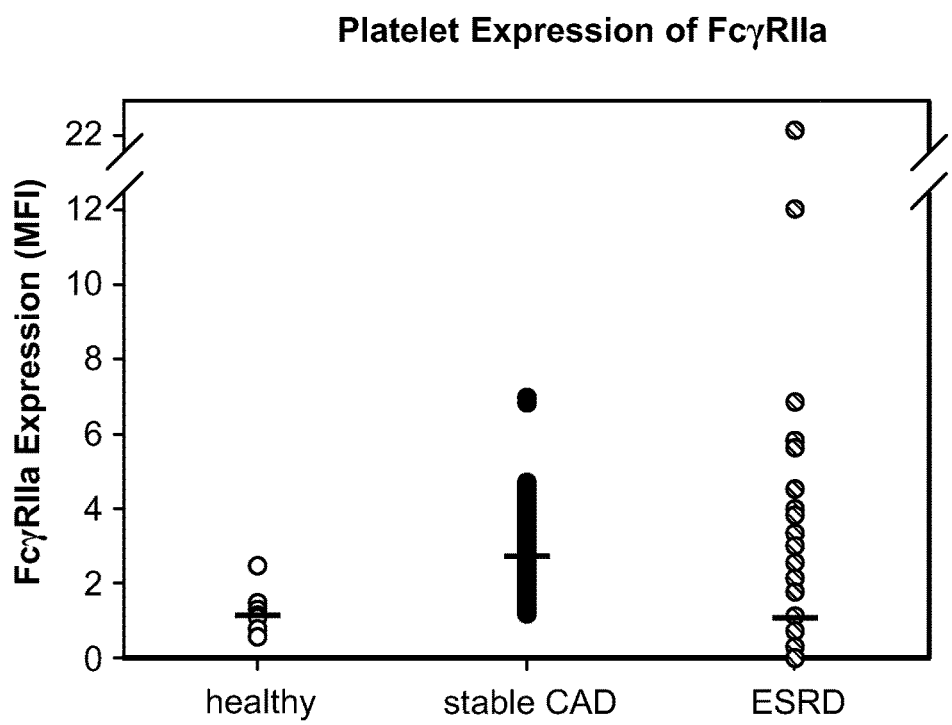
FIGS. 8A and 8B are graphs showing levels of FcγRIIa on platelets of patients having coronary artery disease (CAD) or end stage renal disease (ESRD) relative to healthy controls.
Figures 8B, 9:
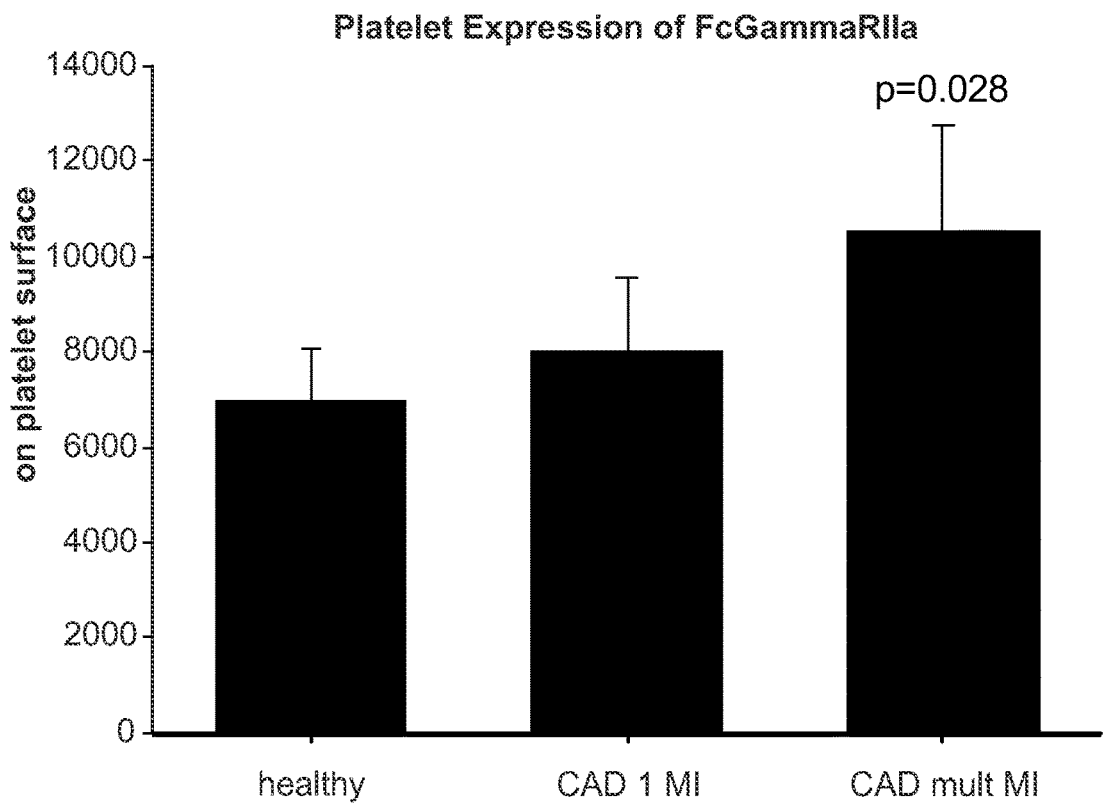
FIG. 9 is a table showing the list of inflammation associated cytokines and growth factors that effect FcγRIIa expression.

As shown in FIG. 8A, platelets from patients with coronary artery disease (CAD) and end stage renal disease (ESRD) express higher levels of FcγRIIa than platelets from healthy controls. As shown in FIG. 8B, platelets from patients with coronary artery disease (CAD) and one or more myocardial infarctions express higher levels of FcγRIIa than platelets from healthy controls. In particular, patients with multiple myocardial infarctions have the highest expression of FcγRIIa and all patients with CAD have higher expression of FcγRIIa.

As shown in FIG. 9, a number of inflammation related cytokines and growth factors influence the expression of FcγRIIa.

Figure 10:
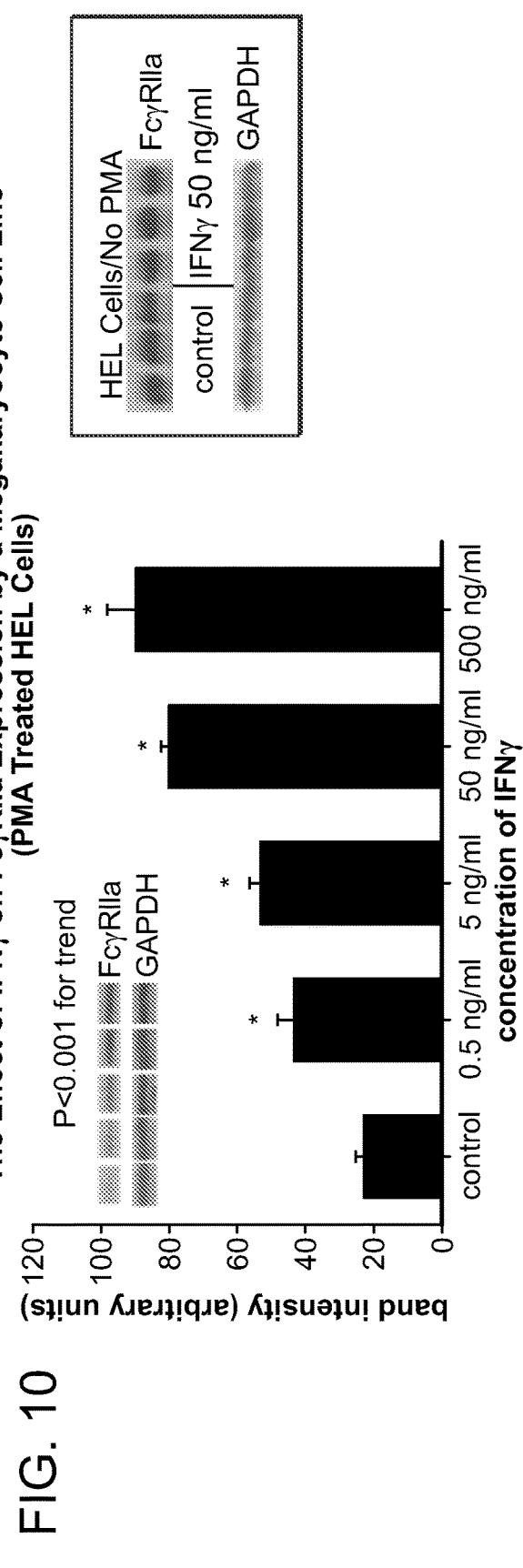
FIG. 10 shows that IFNγ increases the expression of FcγRIIa by megakaryocytes. The graph on the top demonstrates that IFNγ increases the expression of FcγRIIa by a cells that exhibits characteristics of megakaryocytes. The graphs on the lower aspect of the figure show evidence of differentiation of the stem cells into megakaryocytes.
Figure 10:
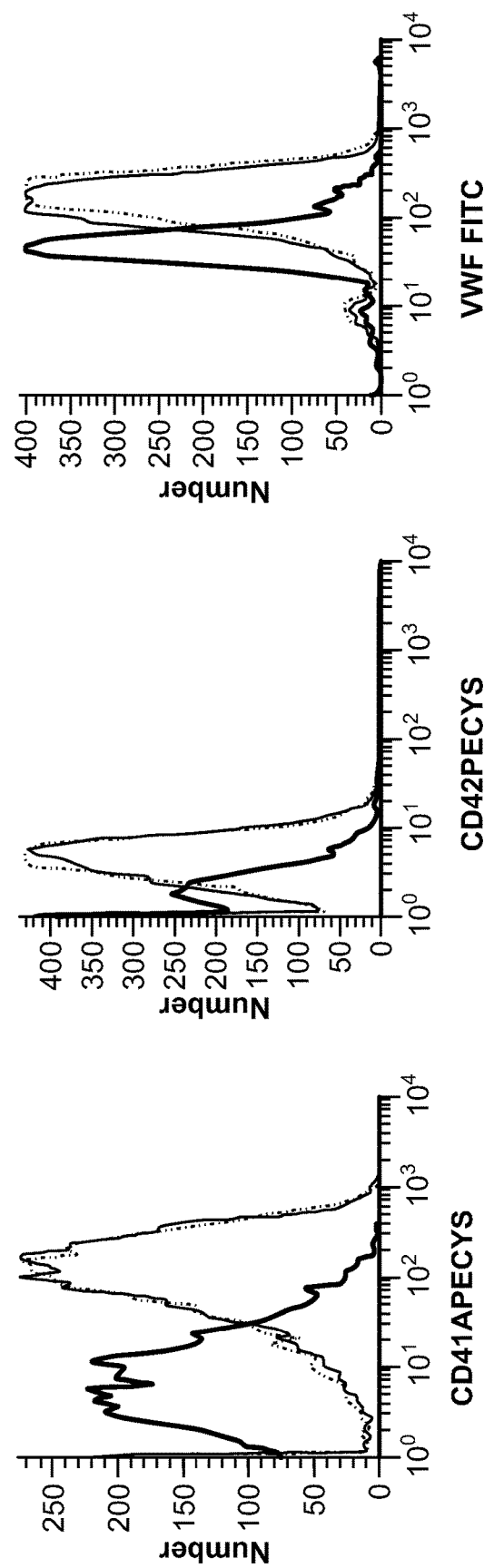

As shown in FIG. 10, IFNγ treatment increases the expression of FcγRIIa by a Megakaryocyte cell line.

Figure 11:
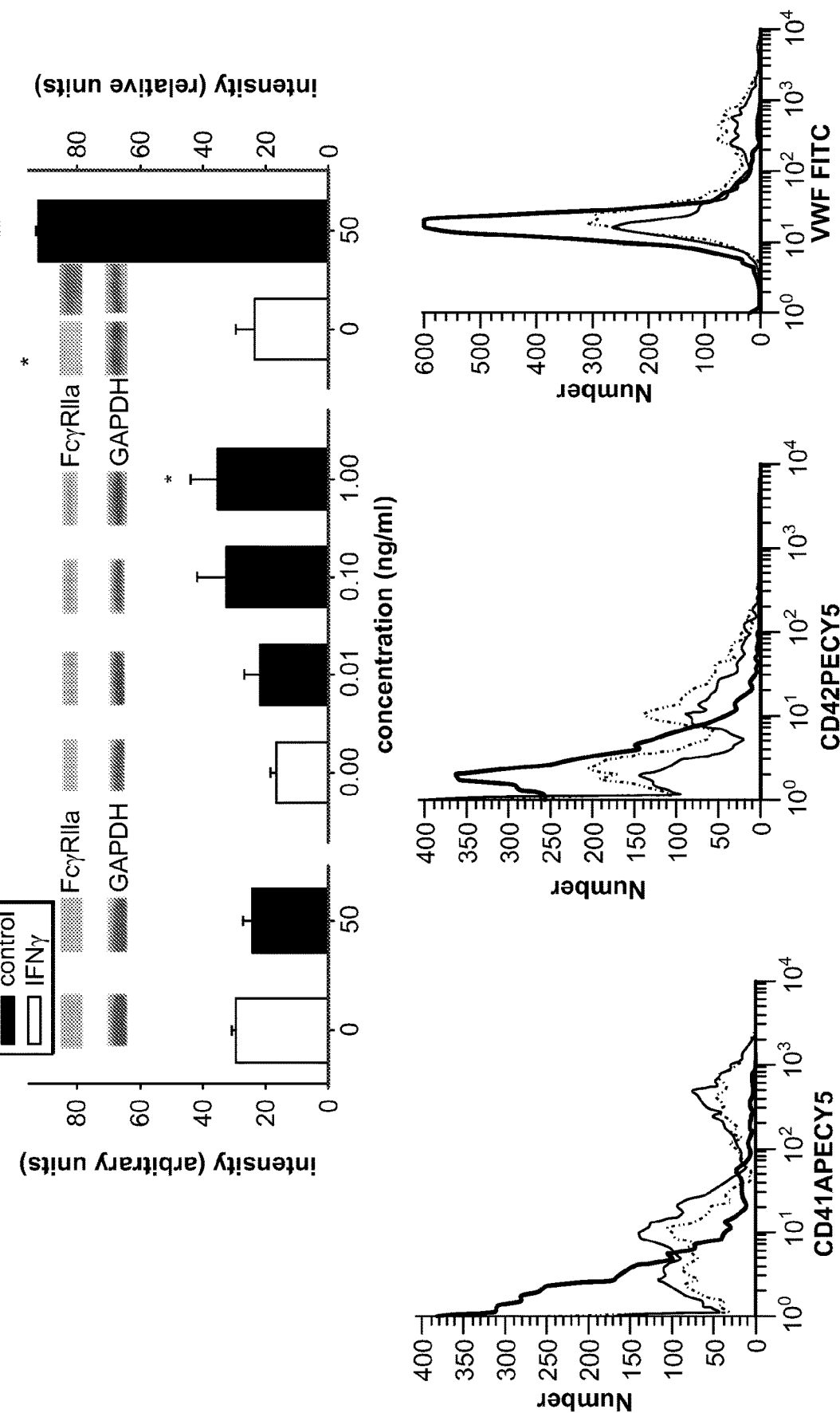
FIG. 11 shows that IFNγ increases the expression of FcγRIIa by human stem cell derived megakaryocytes. The graph on the top demonstrates that IFNγ increases the expression of FcγRIIa by a cell line that exhibits characteristics of megakaryocytes. The graphs on the lower aspect of the figure show evidence of differentiation of the cells into megakaryocytes.

As shown in FIG. 11, IFNγ treatment increases the expression of FcγRIIa by human stem cell derived Megakaryocytes.

Figure 12:
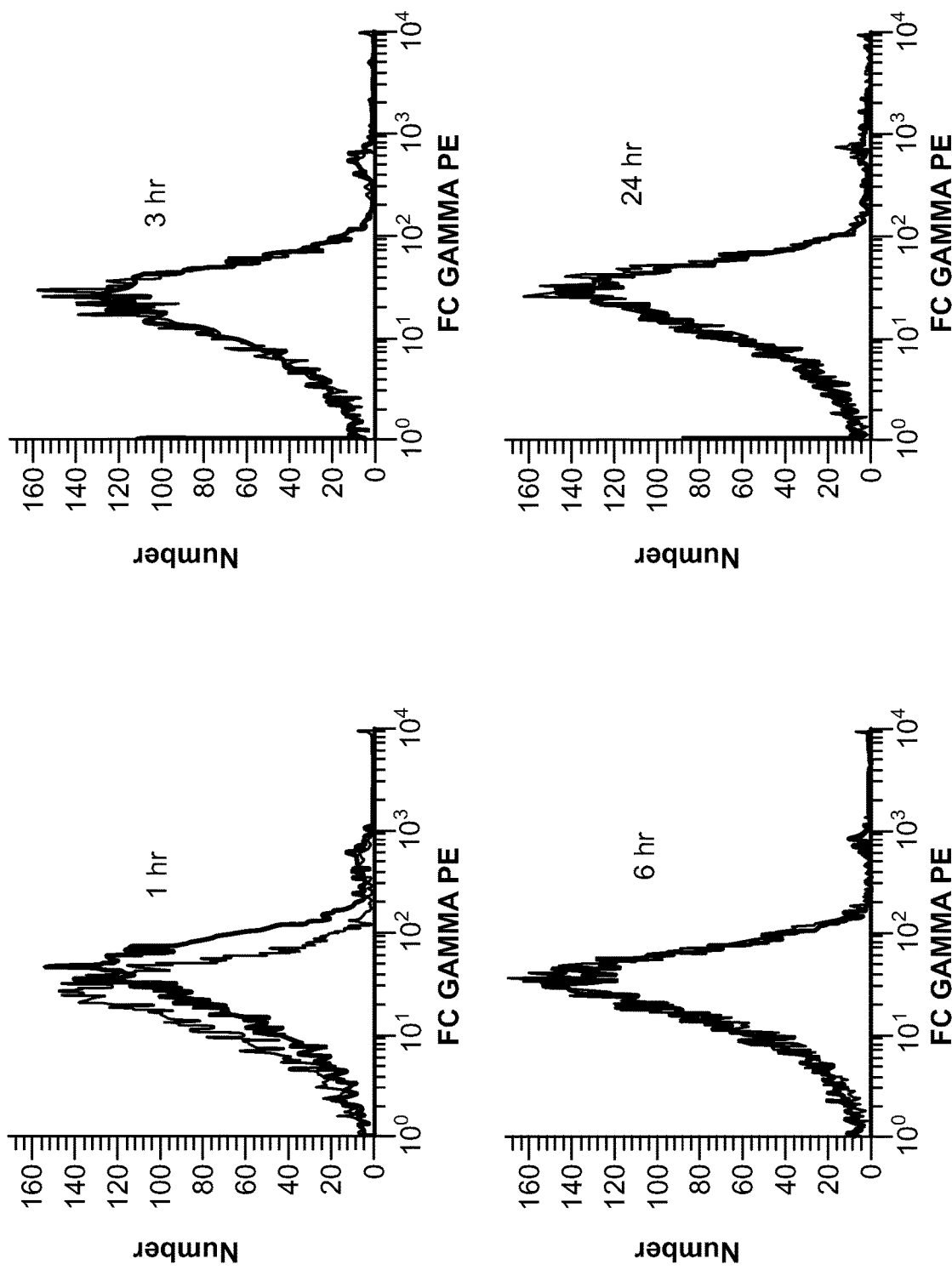
FIG. 12 shows the effects of IFNγ on platelet expression of FcγRIIa.

FIG. 12 shows the effect of IFNγ treatment on platelet expression of FcγRIIa.

Figure 13:
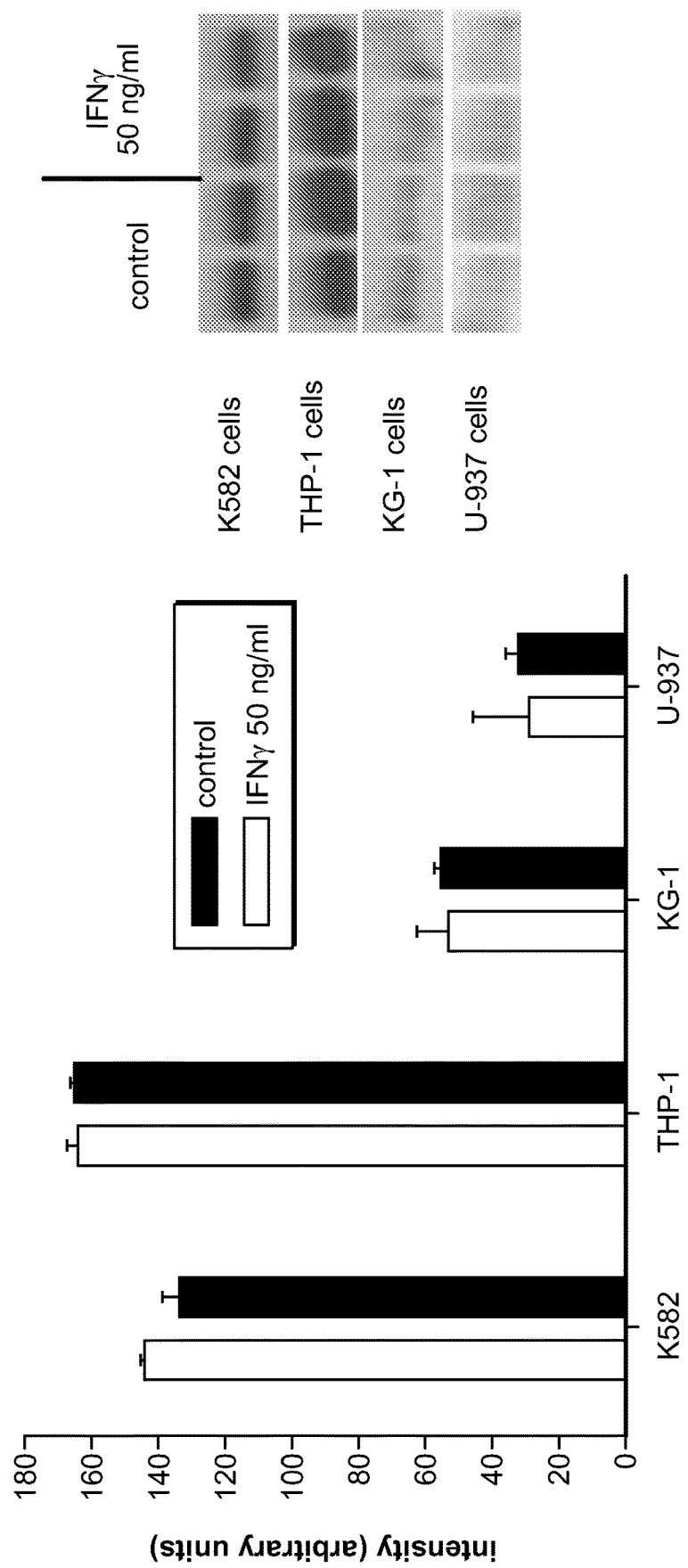
FIG. 13 shows the effects of IFNγ on monocytic and myelocytic cell line expression of FcγRIIa.

FIG. 13 shows the effect of IFNγ treatment on monocytic and myelocytic cell line expression of FcγRIIa.

Figure 14:
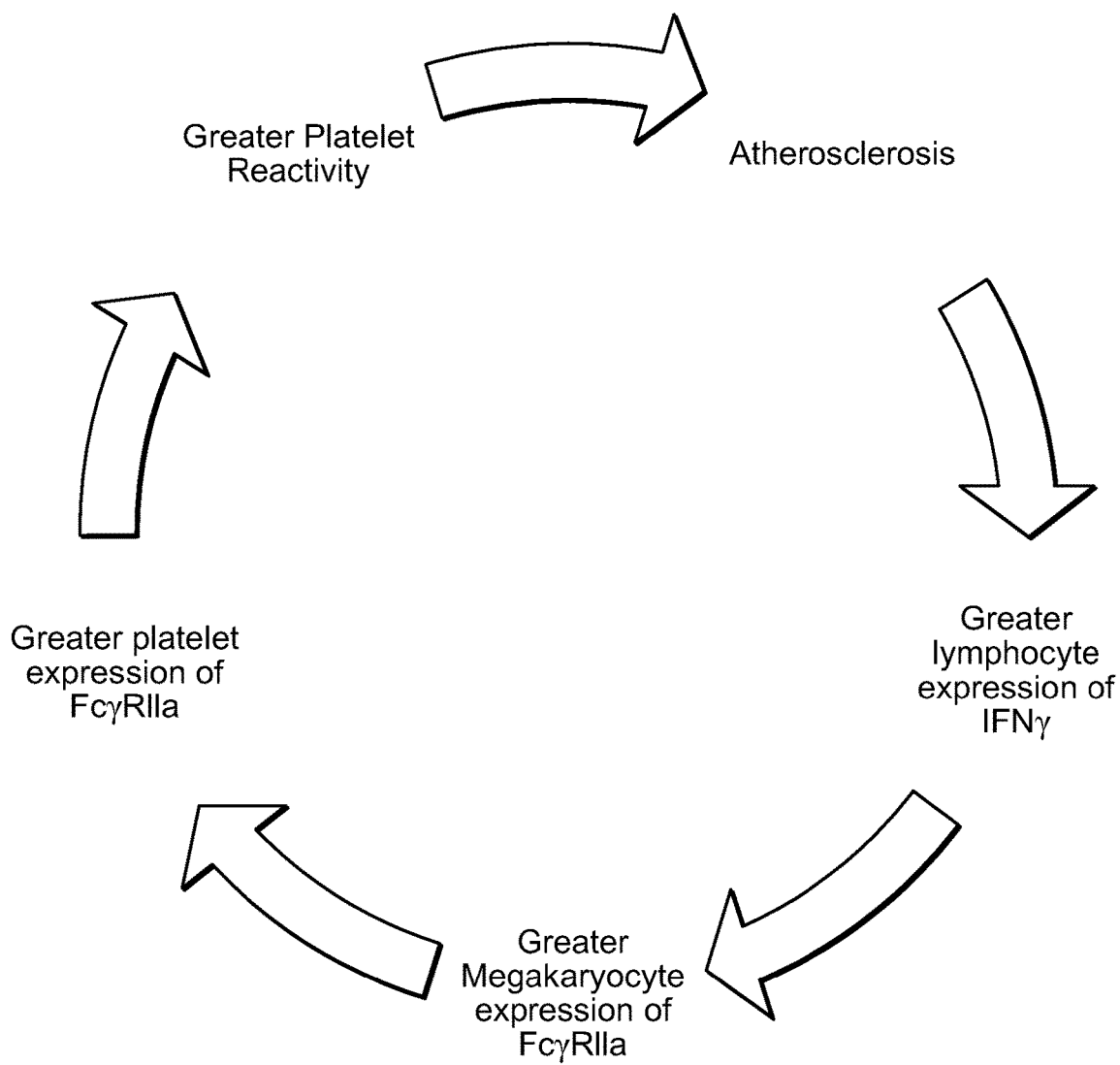
FIG. 14 is a schematic diagram that illustrates the role of interrelation of FcγRIIa, platelet activation, and atherogenesis.

The relationship of FcγRIIa, platelet activation, and atherogenesis is illustrated in FIG. 14.

Figure 15:
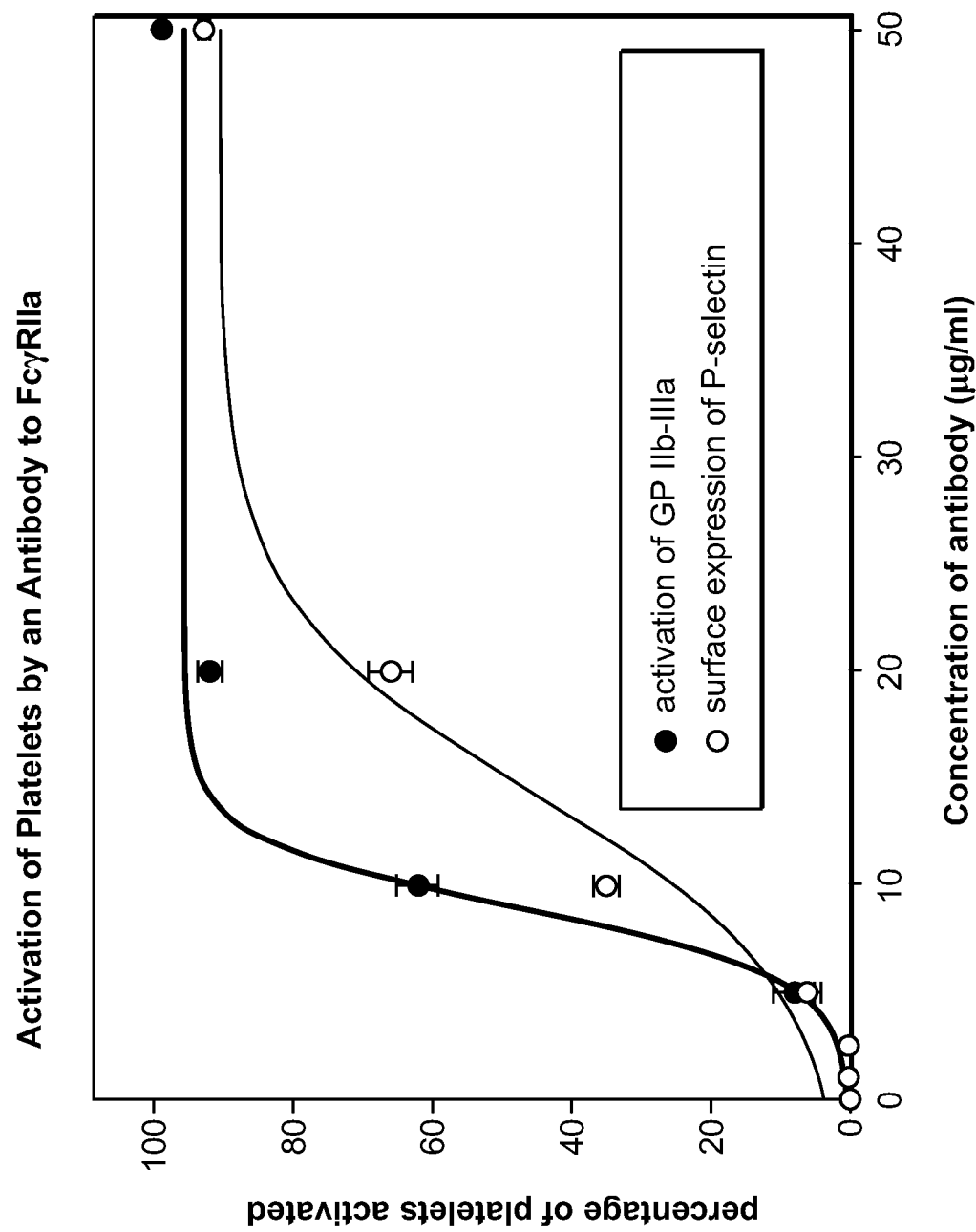
FIG. 15 is a graph showing that an FcγRIIa specific antibody activates platelets.

As shown in FIG. 15, an antibody specific for FcγRIIa is able to cause platelet activation.

Figure 16:
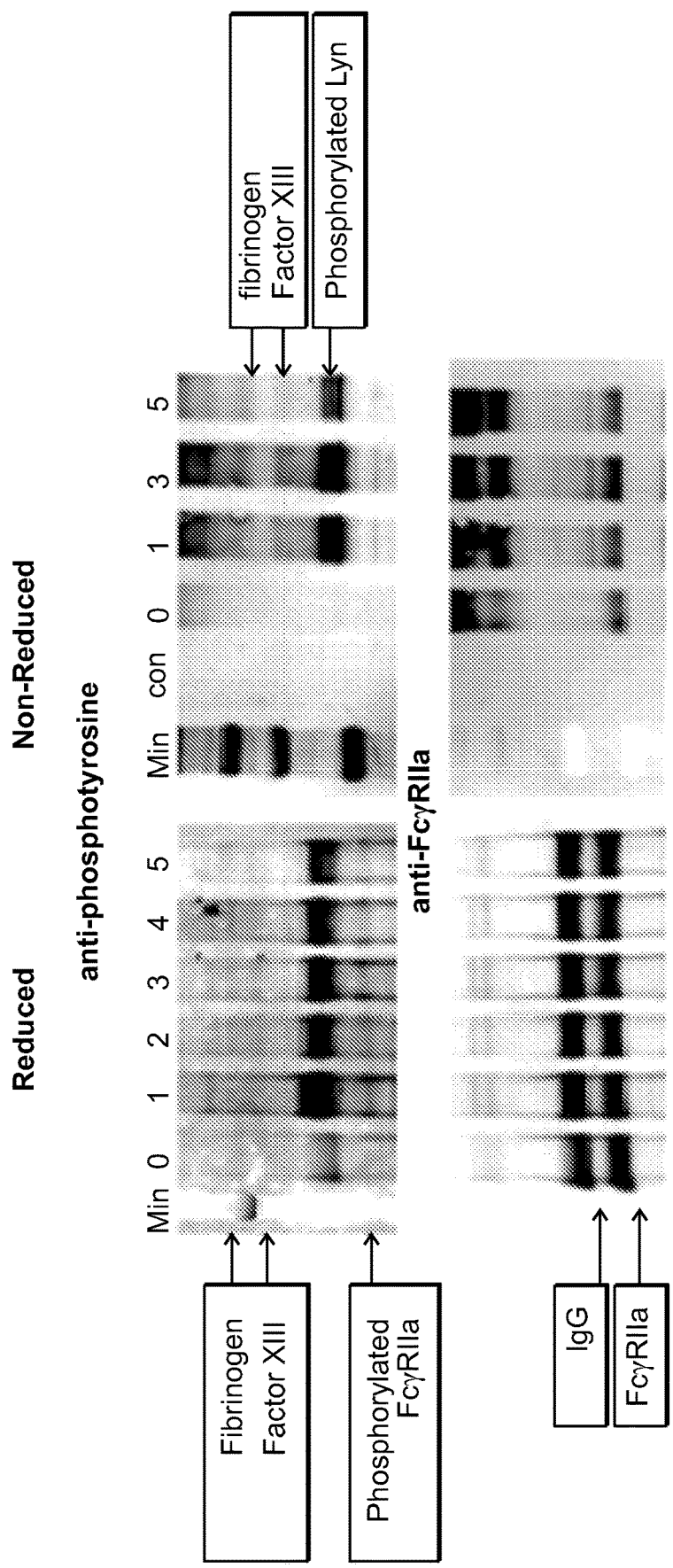
FIG. 16 provides a series of western blots showing FcγRIIa phosphorylation in thrombin activated platelets.
Figure 17:
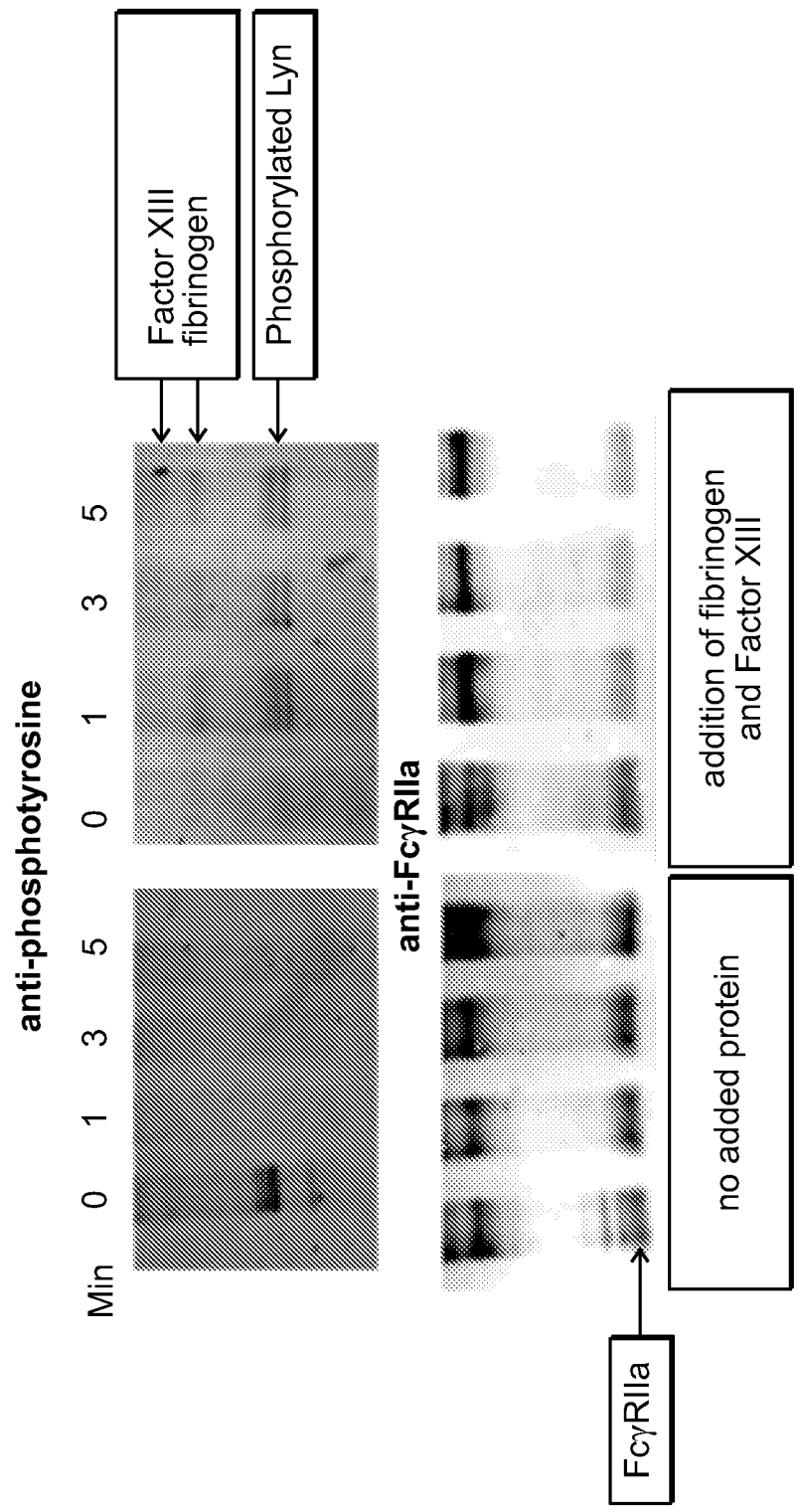
FIG. 17 shows the phosphorylation state of immunoprecipitated FcγRIIa from ADP activated platelets.

As shown in FIGS. 16 and 17, FcγRIIa becomes phosphorylated in thrombin and ADP activated platelets respectively.

Figure 18:
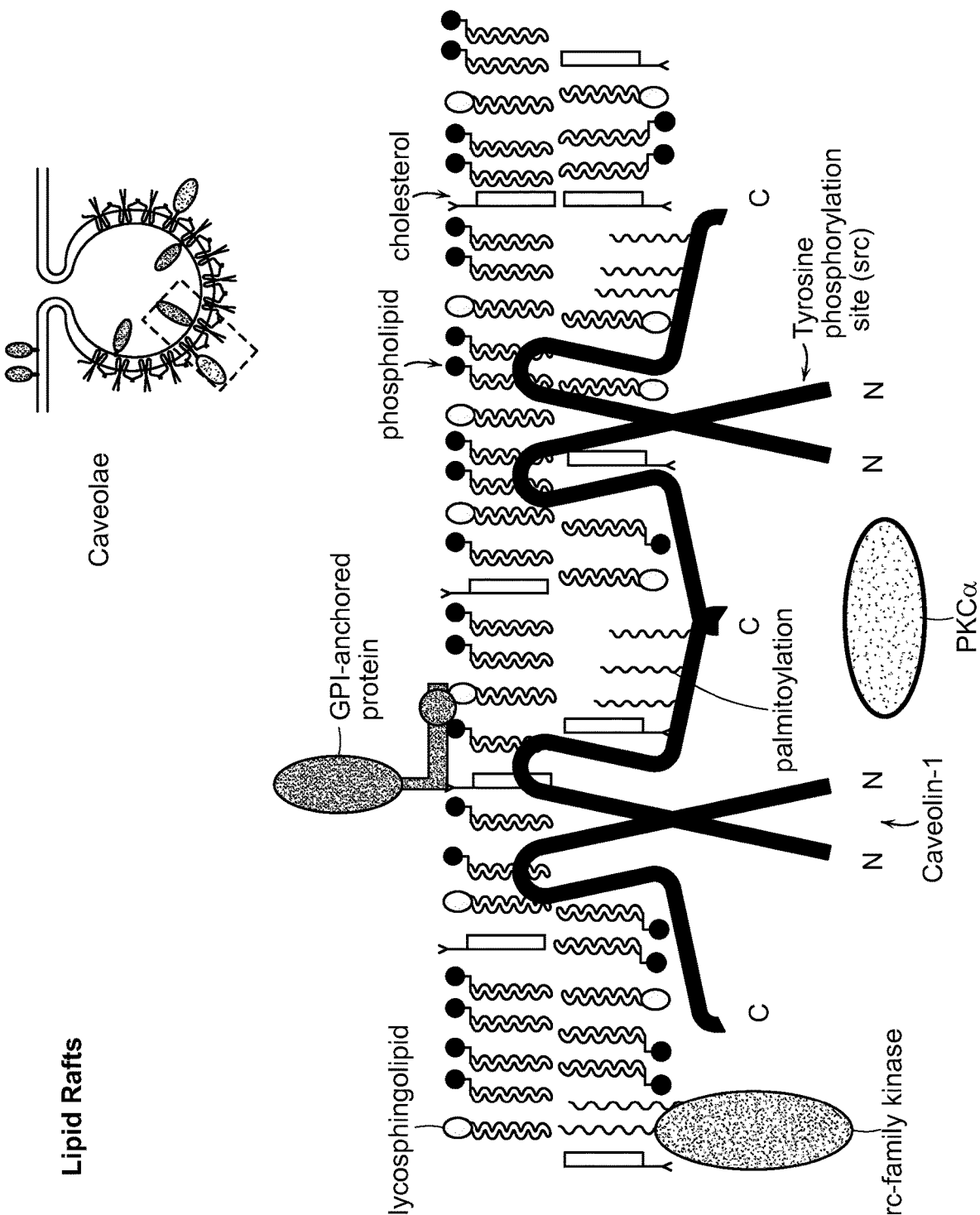
FIG. 18 is an illustration of lipid rafts.
Figure 19A:
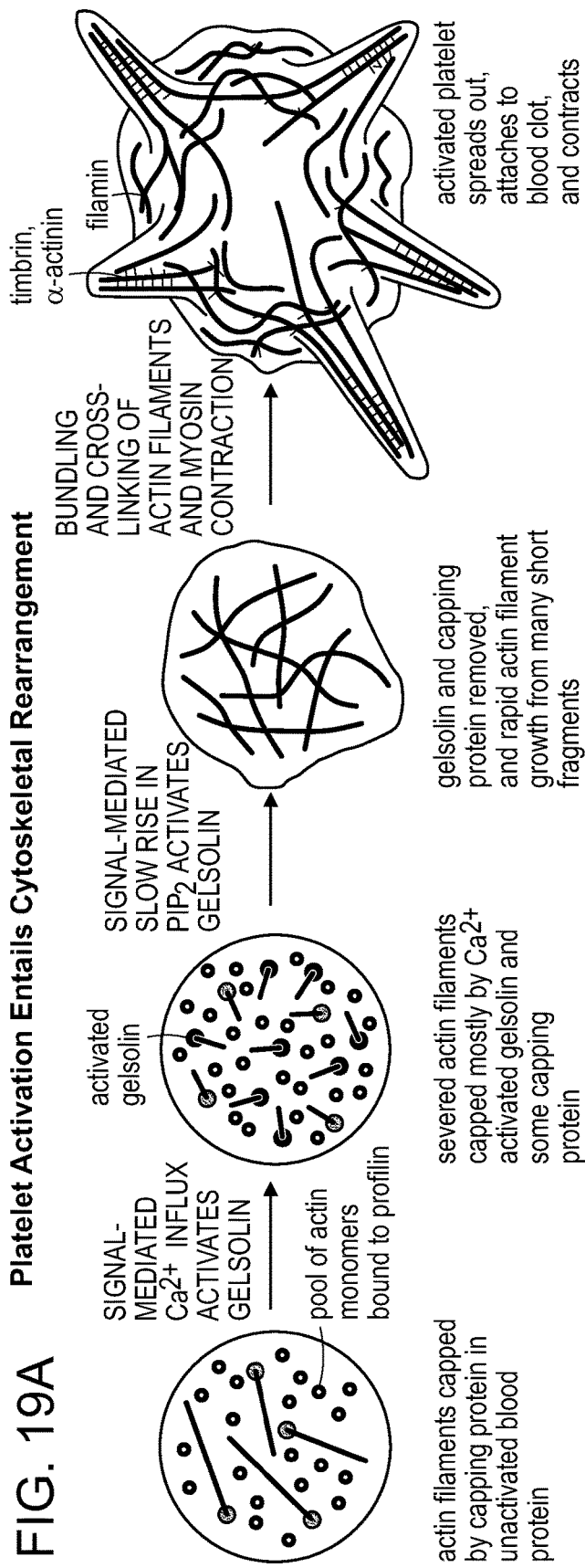
FIG. 19 is an illustration showing the cytoskeletal rearrangement that happens during platelet activation.
Figure 19B:
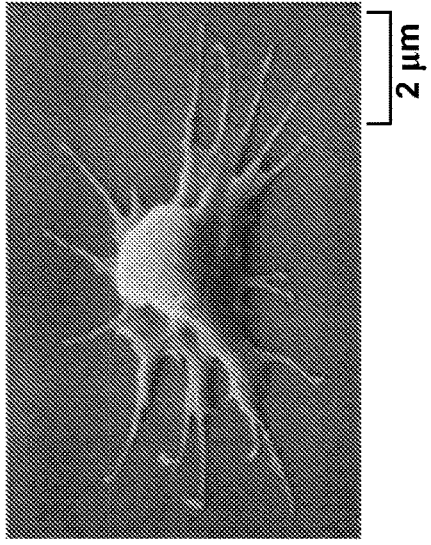
Figure 19C:
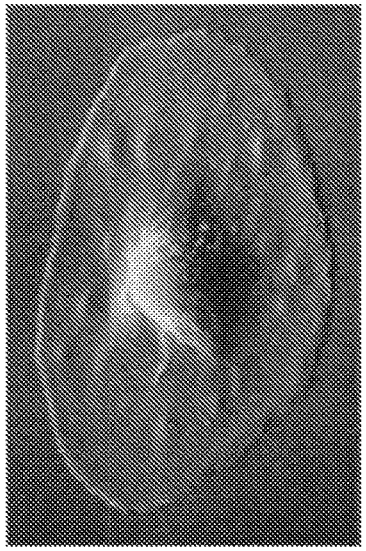
Figure 19D:
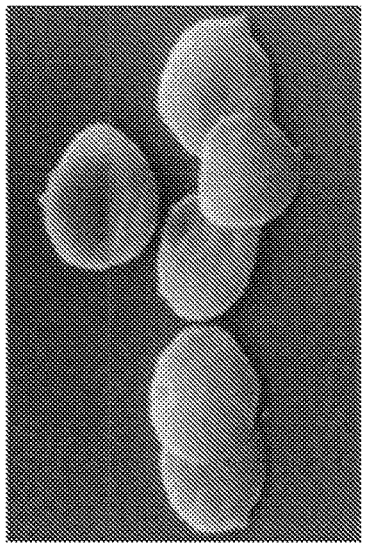

The structure of lipid rafts is illustrated in FIG. 18.

As shown in FIG. 19, platelet activation entails cytoskeletal rearrangement.

Figure 20:
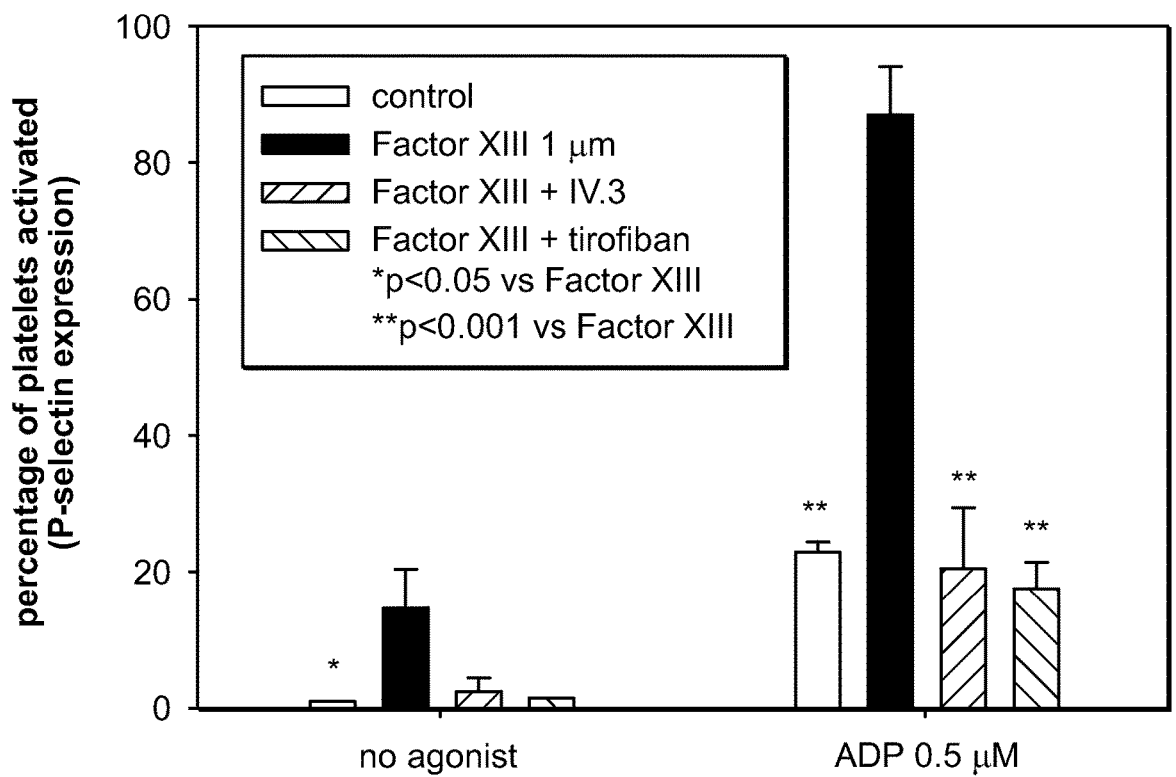
FIG. 20 shows the effect of Coagulation Factor XIII on platelet activation.

FIG. 20 shows the effect of coagulation factor XIII on platelet activation.

Figure 21:
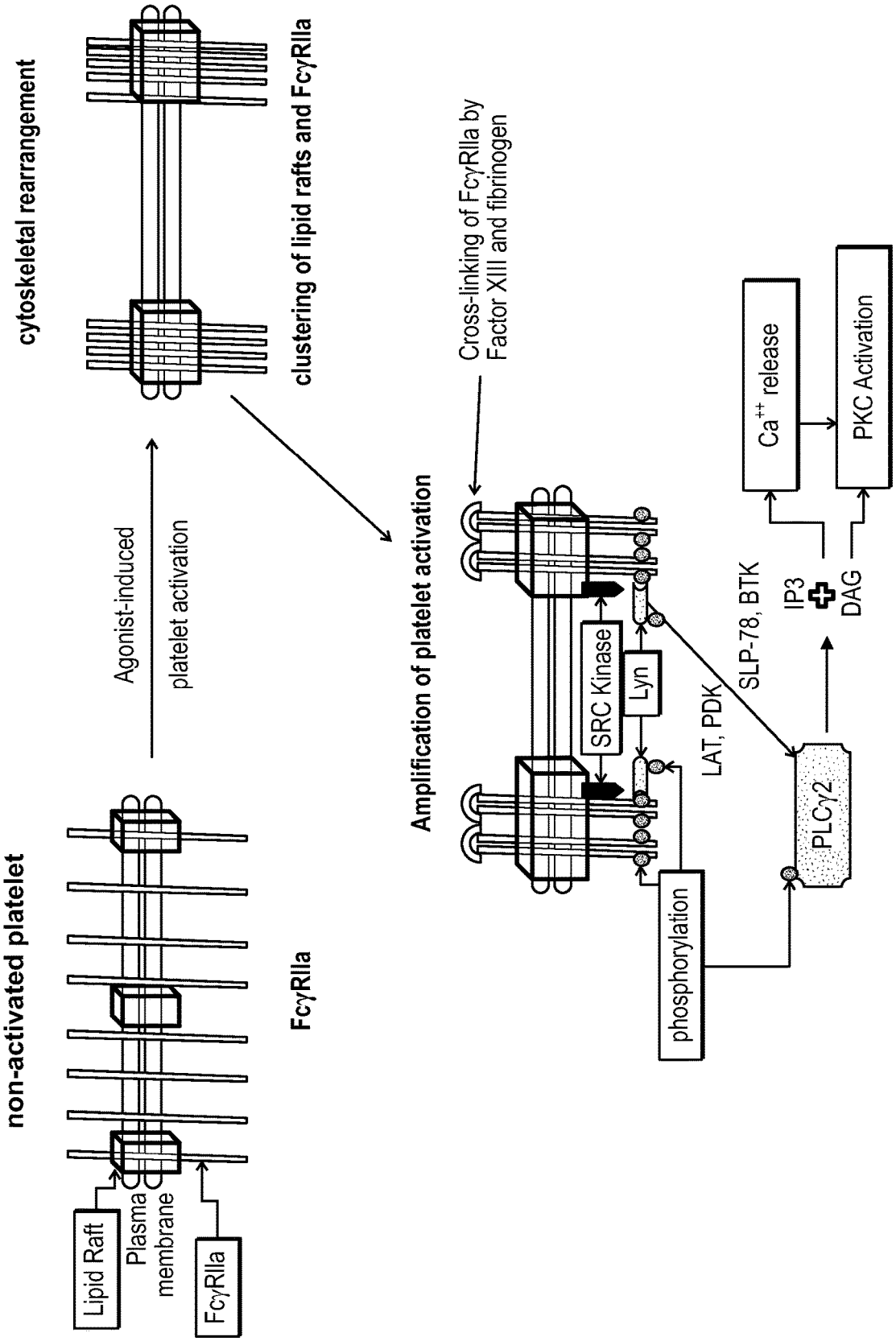
FIG. 21 illustrates the role of FcγRIIa in platelet activation.

The role of FcγRIIa in platelet activation is illustrated in FIG. 21.

The examples presented in this application were performed using the following materials and methods.

Blood Sample Collection

In accordance with a protocol approved by the University of Vermont Institutional Review Board, blood was taken from healthy subjects or from patients with coronary artery disease after they provided written informed consent. Patients with coronary artery disease had a previous myocardial infarction or coronary revascularization plus elevated platelet expression of FcγRIIa and were treated with aspirin but not other antiplatelet or anticoagulant medication. Phlebotomy was performed with a 21 gauge butterfly needle, tourniquets were applied for less than 90 seconds, and the first 3 ml of blood were discarded. Blood (1 ml) for assay of platelet function was anticoagulated with 32 µg/ml of corn trypsin inhibitor (CTI, Haematologic Technologies Inc, Essex Junction, VT), a specific inhibitor of Factor XIIa without effect on other coagulation factors (Rand M D, et al., *Blood* 1996; 88:3432-45), that does not alter the activation of platelets (Schneider D J, et al., *Circulation* 96:2877-83, 1997). Washed platelets were prepared from blood anticoagulated with acid citrate dextrose (ACD, tri-sodium citrate, 0.085 M; citric acid, 0.071 M; glucose 0.1 M, pH 4.5, 1:10 v/v).

Assessment of Platelet Function:

To assess platelet function, 5 µl aliquots of whole blood were added to tubes containing HEPESTyrodes (HT) buffer (5 mM HEPES, 137 mM NaCl, 2.7 mM $NaHCO_3$, 0.36 mM NaH2PO4, 2 mM CaCl2, 4 mM MgCl2, and 5 mM glucose, pH 7.4) and fluorochrome-labeled ligands. Volumes used minimize aggregation of platelets during activation. Activation of platelets was identified by anti-CD62-phycoerythrin (PE, identifies P-selectin) and fluorescein isothiocyanate (FITC)-conjugated PAC-1 (binds to activated GP IIb-IIIa) as described (Serrano F A, et al., *Thromb J* 2007; 5:7; Schneider D J, et al., *Circulation* 96:2877-83, 1997; Kabbani S S, et al., *Circulation* 2001; 104:181-6; Aggarwal A, et al., *Am J Kidney Dis* 2002; 40:315-22; and Schneider D J, et al., *Diabetes Care*, 32:944-9, 2009). Platelet expression of FcγRIIa was quantified with the use of anti-CD32-PE. For both assays (activation and quantification of expression of FcγRIIa) PE-Cy5-anti-CD42b was used as an activation independent marker of platelets. When thrombin or coagulation Factor XIII were used, the peptide GPRP (Gly-Pro-Arg-Pro) was added to prevent polymerization of fibrinogen (Achyuthan K E, et al., *Biochem Biophys Acta* 1986; 872:261-8). Fluorochrome labeled antibodies were from Becton Dickinson (San Jose, CA). Human α-thrombin and coagulation Factor XIII were from Haematologic Technologies Inc (Essex Junction, VT), PAF from EMD Biosciences (Gibbstown, NJ), fibrinogen (>95% pure) from Sigma (St. Louis, MO), and ADP from BioData (Horsham, PA). Convulxin is a collagen-mimetic lectin that binds to GP VI (Clemetson J M, et al., *J Biol Chem* 1999; 274:29019-24, Pentapharm, Basel, Switzerland). The Fab of an antagonist to FcγRIIa (IV.3) was prepared (Pierce Fab preparation kit, Thermo Scientific, Rockford, IL) from IgG produced by hybridoma cells (HB-217 cells, American Tissue Culture Center, Manassas, VA) (Looney, R. J. et al., *J Exp Med* 1986; 163:826-836). The SRC kinase antagonist PP2 (EMD Biosciences) was dissolved in dimethylsulfoxide (DMSO, Sigma). Tirofiban was obtained from Merck Research Laboratories (Whitehouse Station, NJ).

The reaction mixture was incubated for 15 minutes at room temperature without stirring before platelets were fixed and erythrocytes lysed by addition of Optilyse-C solution (Beckman Coulter). Flow cytometric analysis was performed with the use of a Beckman Coulter FC500 (Miami, FL). Platelets were identified on the basis of size (forward and side scatter) and the binding of an activation independent ligand (anti-CD42b). As described, control samples to define a threshold for activation-dependent binding used non-immune IgG (Serrano F A, et al., *Thromb J* 2007; 5:7; Schneider D J, et al., *Circulation* 96:2877-83, 1997; Kabbani S S, et al., *Circulation* 2001; 104:181-6; Aggarwal A, et al., *Am J Kidney Dis* 2002; 40:315-22; and Schneider D J, et al., *Diabetes Care*, 32:944-9, 2009). Activation of platelets is reported as the percentage of platelets that bound an activation dependent ligand, a result that we have shown correlates directly with mean fluorescence intensity (Schneider D J, et al., *Thromb Haemost* 2001; 85:309-13).

Turbidometric platelet aggregation was performed with the use of a PAP-4 aggregometer (BioData, Horsham PA). Maximal aggregation after 4 min was reported. For aggregometry, thrombin receptor agonist peptide (TRAP, Bachem, Torrance, CA) was to mimic effects of thrombin.

Assessment of Platelet Proteins:

Washed platelets ($2\times10^8$ in 0.5 ml) isolated by gel filtration (Sepharose CL-2B, Sigma) from platelet rich plasma (PRP—centrifugation of 140 g×15 min at room temperature) used to demonstrate phosphorylation of FcγRIIa were activated at room temperature without stirring for selected intervals. Whole platelet lysates were prepared by the addition of an equal volume of 2×lysis buffer (2% Nonidet P-401, 300 mM NaCl, 50 mM Tris, 2 mM Na3VO4, halt protease and phosphatase inhibitor cocktail [Pierce Biochemicals], ph 7.3) in an ice bath for 30 min. Lysates to be used for immunoprecipitation were pre-cleared of antibodies by the addition of protein G Dynabeads (Invitrogen, Carlsbad, CA).

Immunoprecipitation was performed overnight at 4° C. with the use of goat anti-CD32A/C (Santa Cruz Biotechnology, Santa Cruz, CA) or a mouse anti-phosphotyrosine conjugated with magnetic beads (4G10, Millipore, Billerica, MA). When anti-CD32A/C was used, antigenantibody complexes were isolated with the use of protein G-coated magnetic beads (Dynabeads, Invitrogen, Carlsbad, CA) for 3 hours. Beads with antigen-antibody complexes were washed once with 0.5×lysis buffer and twice with phosphate buffered saline. Proteins were separated from beads in sample buffer before electrophoresis and wet transfer to Immobilon FL membranes (Millipore, Billerica, MA). Phosphorylation was identified with a mouse anti-phosphotyrosine (clone 4G10, Millipore) or with goat anti-CD32A/C (Santa Cruz Biotechnology, Santa Cruz, CA). Bands were detected with the use of use of a Li-Cor Odyssey Infrared Imaging system (Li-Cor Biosciences, Lincoln, NE) or chemiluminescence (Amersham/General Electric Healthcare, Piscataway, NJ).

Lipid rafts were isolated as described (Lee F A, et al., *f Biol Chem* 2006; 281:39330-8) from washed platelets ($4\times10^8$ in 0.5 ml) that were activated for 90 sec at room temperature without stirring and then lysed by the addition of 2X lipid raft lysis buffer (20 mM Tris, 100 mM NaCl, 60 mM sodium pyrophosphate, 20 mM sodium glycerophosphate, 0.02% w/v sodium azide, 0.025 Triton™ X-100 (2-[4-(2,4,4-trimethylpentan-2-yl) phenoxylethanol), 2 mM sodium vanadate protease inhibitor tablet, pH 8.0). After 30 min on ice, samples were mixed with equal volumes of 80% w/v sucrose and a sucrose gradient was prepared by addition of 5 ml of 36% w/v sucrose followed by 5 ml of 5% w/v. Each sucrose solution contained 0.025% w/v Triton™ X-100 and separation was accomplished by centrifugation (200,000g for 18 hr at 40C). Sequential 1 ml fractions were collected.

Proteomic assessment of proteins co-immunoprecipitated with FcγRIIa was performed by the University of Vermont Proteomics Core (Dwight Matthews, Co-Director). Bands visible after GelCode staining (Pierce Biotechnology, Rockford, IL) were excised, trypsin digested (ProteaseMAX protocol, Promega, Madison, WI) and identified with the use of liquid chromatography-mass spectrometry. High pressure liquid chromatography (Shimadzu, Columbia, MD) was used to separate protein digests on a 100 µm×50 mm column packed with Michrom 3µ C18 AQ (Auburn, CA). Peptides eluted from the column were analyzed with the use of a linear ion trap mass spectrometer (Thermo Scientific, San Jose, CA) fitted with a Michrom Advance electrospray source. Proteins were identified from peptide amino acid sequences that were determined using the Thermo Scientific SEQUEST algorithm.

Confocal Microscopy

Confocal microscopy was performed as described previously (Schneider D J, et al., *J Am Coll Cardiol* 1999; 33:261-6). Platelets exposed to selected conditions were fixed with Optilyse-C for 15 minutes and then pretreated with 1% bovine serum albumin (BSA) in HT buffer for 15 min before incubation with primary antibodies. A primary goat anti-FcγRIIa/CD32a was used to identify FcγRIIa and anti-CD36 was used to identify lipid rafts (Gousset K, et al., J Cell Physiol 2002; 190:117-28). CD36 was chosen to identify lipid rafts because it is differentially associated with lipid rafts located in the platelet plasma membrane (Gousset K, et al., J Cell Physiol 2002; 190:117-28). Platelets separated by centrifugation (1,500 g×10 min) were washed 3 times (HT) before addition of secondary antibodies to identify CD36 (Alexa 488 anti-mouse IgG) and FcγRIIa (Alexa 555 anti-goat IgG). After centrifugation (1,500 g×10 min), platelets were resuspended and applied to a glass microscopic slide for 30 minutes before 2 washes (HT). A cover slip was applied and platelets were imaged with the use of a Zeiss LSM 510 META confocal/scanning laser microscope (Zeiss Microimaging, Thornwood, NY). Control slides with primary antibody alone and secondary antibody alone were used to identify auto fluorescence and non-specific association of secondary antibodies.

Statistical Analysis

Results are means±standard deviation. Significance of differences was assessed with the use of Student's t tests. Significance was identified by p<0.05.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

```
                             SEQUENCE LISTING

Sequence total quantity: 4
SEQ ID NO: 1             moltype = AA  length = 317
FEATURE                  Location/Qualifiers
source                   1..317
                         mol_type = protein
                         organism = Homo sapiens
SEQUENCE: 1
MTMETQMSQN VCPRNLWLLQ PLTVLLLLAS ADSQAAAPPK AVLKLEPPWI NVLQEDSVTL    60
TCQGARSPES DSIQWFHNGN LIPTHTQPSY RFKANNNDSG EYTCQTGQTS LSDPVHLTVL   120
SEWLVLQTPH LEFQEGETIM LRCHSWKDKP LVKVTFFQNG KSQKFSHLDP TFSIPQANHS   180
HSGDYHCTGN IGYTLFSSKP VTITVQVPSM GSSSPMGIIV AVVIATAVAA IVAAVVALIY   240
CRKKRISANS TDPVKAAQFE PPGRQMIAIR KRQLEETNND YETADGGYMT LNPRAPTDDD   300
KNIYLTLPPN DHVNSNN                                                  317

SEQ ID NO: 2             moltype = DNA  length = 954
FEATURE                  Location/Qualifiers
source                   1..954
                         mol_type = genomic DNA
                         organism = Homo sapiens
SEQUENCE: 2
atgactatgg agacccaaat gtctcagaat gtatgtccca gaaacctgtg gctgcttcaa    60
ccattgacag ttttgctgct gctggcttct gcagacagtc aagctgcagc tcccccaaag   120
gctgtgctga aacttgagcc cccgtggatc aacgtgctcc aggaggactc tgtgactctg   180
acatgccagg gggctcgcag ccctgagagc gactccattc agtggttcca caatgggaat   240
ctcattccca cccacacgca gcccagctac aggttcaagg ccaacaacaa tgacagcggg   300
gagtacacgt gccagactgg ccagaccagc ctcagcgacc ctgtgcatct gactgtgctt   360
tccgaatggc tggtgctcca gacccctcac ctggagttcc aggagggaga aaccatcatg   420
ctgaggtgcc acagctggaa ggacaagcct ctggtcaagg tcacattctt ccagaatgga   480
aaatcccaga aattctccca tttggatccc accttctcca tcccacaagc aaaccacagt   540
cacagtggtg attaccactg cacaggaaac ataggctaca cgctgttctc atccaagcct   600
gtgaccatca ctgtccaagt gcccagcatg ggcagctctt caccaatggg gatcattgtg   660
gctgtggtca ttgcgactgc tgtagcagcc attgttgctg ctgtagtggc cttgatctac   720
tgcaggaaaa agcggatttc agccaattcc actgatcctg tgaaggctgc ccaatttgag   780
ccacctggac gtcaaatgat tgccatcaga aagagacaac ttgaagaaac caacaatgac   840
tatgaaacag ctgacggcgg ctacatgact ctgaacccca gggcacctac tgacgatgat   900
aaaaacatct acctgactct tcctcccaac gaccatgtca acagtaataa ctaa          954

SEQ ID NO: 3             moltype = AA  length = 6
FEATURE                  Location/Qualifiers
REGION                   1..6
                         note = Description of Unknown: PAR tethered ligand sequence
source                   1..6
                         mol_type = protein
```

-continued

```
SEQUENCE: 3             organism = synthetic construct
SFLLRN                                                                          6

SEQ ID NO: 4            moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 4
GPRP                                                                            4
```

What is claimed is:

1. A method of treating a selected subject with an anti-thrombotic therapy, the method comprising: administering an anti-thrombotic agent to the selected subject, wherein the subject is selected by detecting a level of copies of FcγRIIa per platelet from the subject and comparing the level of copies of FcγRIIa per platelet from the subject against a level of copies of FcγRIIa per platelet from a healthy individual, wherein a level increased by at least about 1.5 fold of FcγRIIa per platelet identifies the subject as at risk of thrombosis and in need of anti-thrombotic therapy, wherein the anti-thrombotic agent comprises aspirin.

2. The method of claim 1, wherein the level of FcγRIIa is determined using an FcγRIIa specific reagent.

3. The method of claim 2, wherein the FcγRIIa specific reagent is an antibody or antigen binding fragment thereof.

4. The method of claim 1, wherein the level of platelet FcγRIIa is determined using an assay selected from the group consisting of flow cytometry, immunoassay, ELISA, western blotting, and radioimmunoassay.

5. The method of claim 1, wherein the level of FcγRIIa is determined using fluorometric or colorimetric assay.

6. The method of claim 1, wherein the level of FcγRIIa is determined using flow cytometry.

7. The method of claim 1, wherein the increased level of copies is at least about 2-5 fold of FcγRIIa per platelet.

8. The method of claim 1, wherein the increased level of copies is at least about 5 fold of FcγRIIa per platelet.

9. The method of claim 1, wherein the increased level of copies is at least about 10 fold of FcγRIIa per platelet.

10. The method of claim 1, wherein the anti-thrombotic therapy further comprises a component selected from the group consisting of an Adenosine diphosphate (ADP) receptor antagonist, a Protease-activated receptor (PAR) antagonist, and combinations thereof.

11. The method of claim 10, wherein the component is one or more of prasugrel, ticagrelor, clopidogrel, and vorapaxar.

12. The method of claim 1, wherein the anti-thrombotic therapy further comprises an effective amount of an agent that inhibits FcγRIIa activation, thereby inhibiting platelet activation.

13. The method of claim 1, wherein the anti-thrombotic therapy further comprises an effective amount of an agent that inhibits FcγRIIa activation, thereby inhibiting platelet activation, and the agent is selected from the group consisting of an inhibitory nucleic acid, and an antibody or antigen-binding fragment thereof.

14. The method of claim 13, wherein the agent is an inhibitory nucleic acid selected from the group consisting of an antisense molecule, an shRNA, and an siRNA.

15. The method of claim 13, wherein the agent is an inhibitory nucleic acid and the inhibitory nucleic acid reduces the levels of FcγRIIa in megakaryocytes.

16. The method of claim 1, further comprising the step of detecting the presence or absence of a secondary marker in the subject, wherein the subject is additionally selected for treatment based on the presence or absence of a secondary marker in the subject.

17. The method of claim 1, wherein the level of copies of FcγRIIa per platelet from a healthy individual is determined based on a set of individuals who are disease-free.

18. The method of claim 1, wherein the level of copies of FcγRIIa per platelet from a healthy individual is determined based on a set of individuals who do not have reactive platelets.

19. The method of claim 1, wherein the level of copies of FcγRIIa per platelet from a healthy individual is determined based on a historical measurement from the subject.

* * * * *

UNITED STATES PATENT AND TRADEMARK OFFICE
CERTIFICATE OF CORRECTION

Page 1 of 1

PATENT NO. : 12,253,520 B2
APPLICATION NO. : 18/353683
DATED : March 18, 2025
INVENTOR(S) : David Schneider It is certified that error appears in the above-identified patent and that said Letters Patent is hereby corrected as shown below:

In the Specification

Column 16, Line 35, "APCI-(MS)$^a$" should be --APCI-(MS)$^n$--.

Column 16, Line 36, "APPI-(MS)$_a$" should be --APPI-(MA)$_n$--.

Column 23, Line 59, "phenoxylethanol" should be --phenoxy]ethanol--.

Column 24, Line 54, "between and" should be --between 10 and--.

Column 32, Line 42, "al., $f$" should be --al., J--.

Column 32, Line 49, "phenoxylethanol" should be --phenoxy]ethanol--.

Signed and Sealed this
Fifth Day of August, 2025

Coke Morgan Stewart
*Acting Director of the United States Patent and Trademark Office*